(12) United States Patent
Tidmarsh et al.

(10) Patent No.: US 7,001,888 B2
(45) Date of Patent: Feb. 21, 2006

(54) COMPOSITIONS AND METHODS FOR TREATING CANCER

(75) Inventors: George Tidmarsh, Portola Valley, CA (US); Mark Matteucci, Portola Valley, CA (US); Photon Rao, Millbrae, CA (US)

(73) Assignee: Threshold Pharmaceuticals, Inc., Redwood City, CA (US)

( * ) Notice: Subject to any disclaimer, the term of this patent is extended or adjusted under 35 U.S.C. 154(b) by 0 days.

(21) Appl. No.: 10/402,778

(22) Filed: Mar. 28, 2003

(65) Prior Publication Data

US 2004/0029815 A1    Feb. 12, 2004

Related U.S. Application Data

(60) Provisional application No. 60/429,287, filed on Mar. 29, 2002.

(51) Int. Cl.
 *A61K 31/70* (2006.01)
 *A61K 31/7028* (2006.01)
 *A61K 51/00* (2006.01)
(52) U.S. Cl. ................................ 514/23; 514/25
(58) Field of Classification Search .................. 514/23, 514/25; 424/1.73
 See application file for complete search history.

(56) References Cited

U.S. PATENT DOCUMENTS

| | | | |
|---|---|---|---|
| 3,694,428 A | 9/1972 | Hardegger et al. | |
| 3,940,383 A | 2/1976 | Fujiwara et al. | |
| 4,720,543 A | 1/1988 | McPherson et al. | |
| 4,895,936 A * | 1/1990 | Talebian et al. | 536/17.1 |
| 5,057,301 A | 10/1991 | Wilbur et al. | |
| 5,565,434 A | 10/1996 | Barfknecht et al. | |
| 5,621,002 A | 4/1997 | Bosslet et al. | |
| 5,622,936 A | 4/1997 | Wiessler et al. | |
| 6,037,336 A * | 3/2000 | Hausheer et al. | 514/102 |
| 6,489,302 B1 | 12/2002 | Wiessler et al. | |
| 6,548,484 B1 | 4/2003 | Christian | |

FOREIGN PATENT DOCUMENTS

| | | | |
|---|---|---|---|
| WO | WO 99-20316 | * | 4/1999 |
| WO | WO 99/20316 A1 | | 4/1999 |
| WO | WO 02/58741 A2 | | 8/2002 |

OTHER PUBLICATIONS

Tanaka et al. (JP 38007735 (Abstract Only)) (Abstract Sent.).*
Fowler et al. (Journal of Labelled Compounds and Radiopharmaceuticals (1979), 16 (1, Second Int. Symp: Radiopharm.), 7-9) (Abstract Sent.). . .*
Briasoulis, E. et al. (2000). "Phase I Trial of 6-Hour Infusion of Glufosfamide, a New Alkylating Agent With Potentially Enhanced Selectivity for Tumors That Overexpress Transmembrane Glucose Transporters: A Study of the European Organization for Research and Treatment of Cancer Early Clinical Studies Group," *Journal of Clinical Oncology* 18(20):3535-3544.
Cantuaria, G. et al. (2000). "Antitumor Activity of a Novel Glyco-Nitric Oxide Conjugate in Ovarian Carcinoma," *Cancer* 88(2):381-388.
Hou, Y. et al. (2001). "The synthesis and cytotoxicity of fructose-1-SNAP, a novel fructose conjugated S-nitroso nitric oxide donor," *Tetrahedron Letters* 42:825-829.
Ramirez, J. et al. (1996). "Glyco-S-Nitrosothiols, A Novel Class of No-Donor Compounds," *Bioorganic & Medicinal Chemistry Letters* 6(21):2575-2580.
Seker, H. et al. "Mechanistic aspects of the cytotoxic activity of glufosfamide, a new tumour therapeutic agent," British Journal of Cancer 82(3):629-634.
Veyhl, M. et al. (1998). "Transport of the new chemotherapeutic agent beta-D-glucosylisophosphoramide mustard (D-19575) into tumor cells is mediated by the Na+-D-glucose cotransporter SAAT1," *Proc. Natl. Acad. Sci.* 95:2914-2919.

* cited by examiner

*Primary Examiner*—Samuel Barts
*Assistant Examiner*—Michael C. Henry
(74) *Attorney, Agent, or Firm*—Kevin R. Kaster; Vandana Date; Mark H. Hopkins

(57) ABSTRACT

Methods and compositions are provided for the treatment of cancer that take advantage of the increased uptake of glucose-anti-neoplastic agent conjugates in cancer cells relative to normal cells.

8 Claims, 1 Drawing Sheet

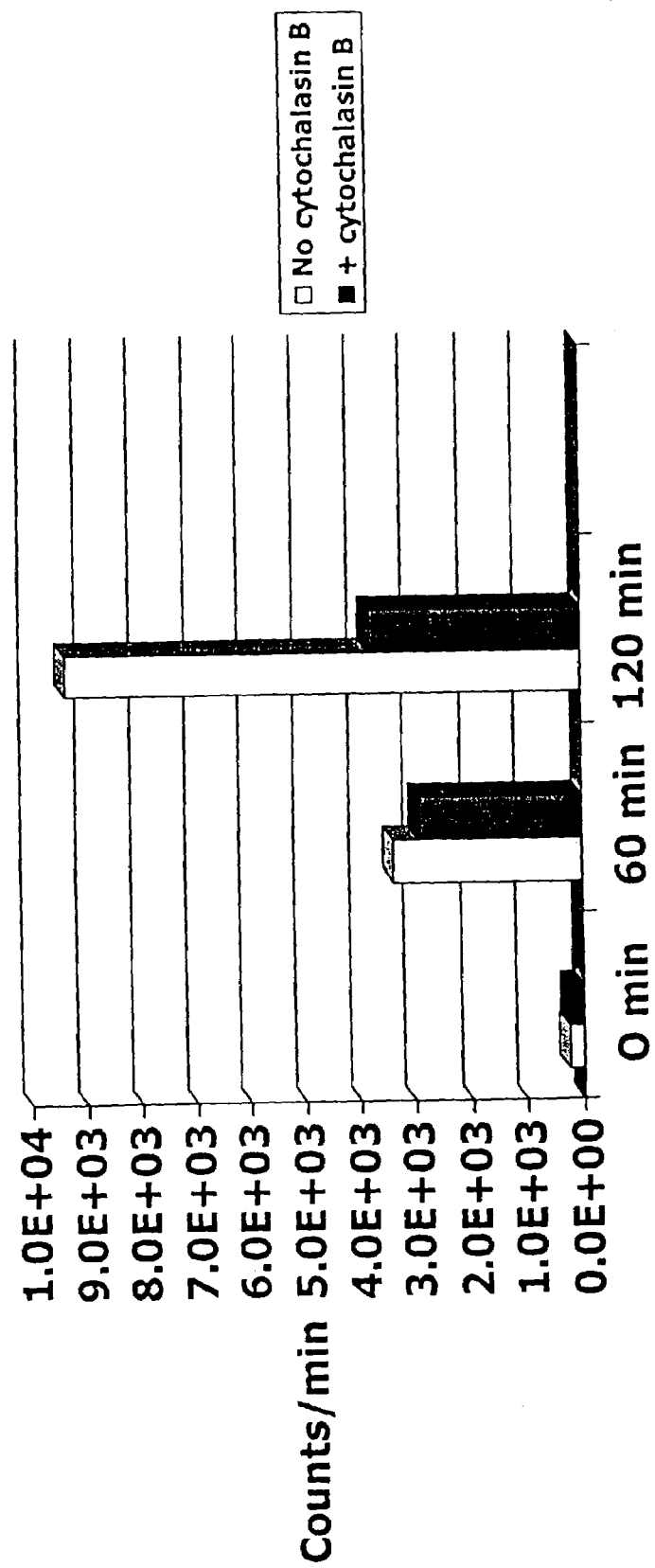

COMPOSITIONS AND METHODS FOR TREATING CANCER

CROSS-REFERENCES TO RELATED APPLICATIONS

This application claims priority to U.S. provisional patent application Ser. No. 60/429,287, filed Mar. 29, 2002, incorporated herein by reference.

BACKGROUND OF THE INVENTION

The term "cancer" generally refers to any of a group of more than 100 diseases caused by the uncontrolled growth of abnormal cells. Cancer can take the form of solid tumors and lymphomas, and non-solid cancers such as leukemia. Unlike normal cells, which reproduce until maturation and then only as necessary to replace wounded cells, cancer cells can grow and divide endlessly, crowding out nearby cells and eventually spreading to other parts of the body.

The principal problem of cancer chemotherapy is achieving good therapeutic indices for the compounds administered to kill the tumor cells. In general, drugs and radiation used to kill cancer cells are also toxic to cells of normal tissue, and so side effects are often severe. The majority of drug-mediated cancer therapies rely on drugs that selectively poison dividing cells. These drugs can be effective, because cancer cells generally divide more frequently than normal cells. Unfortunately, however, there are exceptions to this rule in most cancers, which means that such drugs almost inevitably are unable to kill all cells in a tumor. Moreover, even for drugs that act on mechanisms specific to cancer cells, there are, in the majority of patients, cancer cells not killed by administration of the drug.

While specific proteins can confer drug resistance to a cancer cell, such as the proteins responsible for the multiple drug resistance ("MDR") phenotype, the very nature of the tumor formed by solid cancers, particularly its vascular architecture, contributes significantly to the ability of the cancer to survive drug therapy. As a tumor grows, it requires a blood supply and the growth of new vasculature. The new vasculature that supports the tumor growth is, not surprisingly given the uncontrolled growth that characterizes most cancers, highly disordered, leaving significant portions of the tumor under-vascularized, and the vascularized portions of the tumor subject to intermittent blockage. Because the vasculature delivers oxygen (and chemotherapeutic agents) to cells, tumors therefore typically contain "hypoxic" regions, regions in which the oxygen concentration is significantly lower than in the vast majority of normal tissues and where there may be poor delivery of chemotherapeutic agents.

Oxygen is critical in the supply of energy to a cell in the form of ATP produced by mitochondrial action. A cell's only other source of ATP in the amounts needed to support the cell is from anaerobic glycolysis. Given the demand for ATP in cell division and the hypoxic nature of tumors, it is therefore not surprising that many cancers exhibit, relative to normal cells, increased glycolysis. This attribute of cancer cells was described in the reference Dickens, 1943, *Cancer Research* 3:73, which reported "the typical intact cancer cell exhibits an unusual ability to utilize glucose by the process of anaerobic glycolysis through lactate".

Given the increased glycolysis in cancer cells relative to normal cells, scientists questioned whether inhibition of anaerobic glycolysis by metabolic poisons would preferentially target cancer cells. The compound 2-deoxy-D-glucose (also known and referred to herein as 2-deoxyglucose and 2-DG) is such a metabolic poison. 2-DG inhibits glycolysis in cancer cells, as reported in the reference Woodward, 1954, *Cancer Res.* 14:599–605. However, while many cell-based and animal studies of 2-DG as an anti-cancer agent have been conducted, both as a single agent and in combination with other anti-cancer drugs and/or radiation, the compound has not been approved by any regulatory agency for use in the treatment of cancer. See Yamada, 1999, *Cancer Chemother. Pharmacol.* 44(1):59–64; Reinhold, September 2000, *Oncol. Rep.*, 7(5):1093–97; Mese, March 2001, *Anticancer Res.* 21:1029–33; Lampidis, 2 Mar. 2001, PCT WO 01/82926, Yeung, 11 Dec. 2001, PCT WO 02/58741; and Pitha, Mar. 21, 2002, U.S. patent publication No. 20020035071.

There could be a significant therapeutic benefit from cytotoxic compounds that preferentially target cancer cells based on increased glycolysis. Because cancer cells are known to have, relative to normal cells, increased production of glucose transporters, including GLUT1 and GLUT3, one could attempt to target glucose transport in cancer chemotherapy. While a number of known anti-cancer agents have a structure that can be described as a glucose moiety attached to a cytotoxic agent, and so might be substrates for GLUT1 and/or GLUT3, none of these agents has been widely used with great success to treat cancer.

One such compound, the naturally occurring compound streptozotocin [2-deoxy-2-(3-methyl-3-nitroso-ureido)-D-glucose] is an antibiotic and anti-mitotic compound produced by *Streptomyces achromogenes* (see also U.S. Pat. No. 3,694,428). In streptozotocin, a cytotoxic N-nitroso urea group is attached to the 2 position of glucosamine. The compound is relatively unstable in that the cytotoxic moiety is readily released from the compound in the presence of water. The compound appears to be transported into cells by the glucose transporter GLUT2, which may account for its toxicity to pancreatic islet cells. A limited number of streptozotocin analogs have also been prepared (see U.S. Pat. No. 3,940,383). However, neither streptozotocin nor its analogs has found any significant use in anti-cancer therapies.

Glufosfamide (beta-D-glucosyl-ifosfamide mustard) is another anti-cancer agent that can be described as a cytotoxic agent linked to a glucose moiety. This compound contains the cytotoxic agent ifosfamide coupled to glucose via an ester linkage at the oxygen atom at the 1-position of glucose (see U.S. Pat. No. 5,622,936). The compound has been described as having been made in an effort to target the tumor's need for energy as a means to enhance uptake of ifosfamide into cancer cells (see the website of the dkfz, 14 Jan. 2003, www.toxea.de). The compound has been reported to be subject to cell surface glucose transport, via the SAAT1 receptor. Like streptozotocin, however, glufosfamide is relatively unstable, both chemically and enzymatically, ensuring that ifosfamide will be cleaved from the glucose after administration. Such cleavage could take place in the plasma, by the action of serum esterases, or in the cell, allowing the ifosfamide potentially to diffuse from the cell, which in either event could lead to increased toxicity and/or decreased efficacy.

The glyco-S-nitrosothiols are likewise relatively unstable compounds that can be described as cytotoxic agents linked to sugars. These compounds have been described as targeting tumor cells that over-express GLUT1 preferentially (see Ramirez et al., 1996, *Bioorg. Med. Chem. Lett.* 6(21): 2575–2580; and Cantuaria et al., 15 Jan. 2000, *Cancer* 88(2): 381–388). One glyco-S-nitrosothiol called 2gluSNAP has a structure in which a nitric oxide donating cytotoxic moiety (S-nitroso-N-acetyl-penicillamine) is linked to 2-deoxyglucosamine at the 2 position via an amide bond. The resulting compound is unstable, which can result in release of the cytotoxic nitric oxide before entry into the targeted cell or diffusion out of the targeted cell.

Compounds characterized as single photon-emitting radiotracers that contain a glucose moiety linked to a single photon-emitting moiety via a heterocyclic, hydrocarbon, or aromatic group have been described as allegedly useful for the diagnosis and treatment of cancer (see PCT publication No. WO 99/20316). These compounds include, for example, 2-O-(3'-iodobenzyl)-D-glucose and N-(4'-iodobenzyl)-D-glucosamine.

Compounds characterized as prodrug forms of pharmacologically active substances, including anti-cancer agents, and that contain a glucose or other sugar moiety linked to a pharmacologically active agent at the 1 position either directly or through a self-immolative spacer have been described (see U.S. Pat. No. 5,621,002) as substrates for human glycosidases without indication of whether the glucose moiety contributed to the specificity of the prodrug for a cancer cell.

Thus, while compounds have been made that contain a cytotoxic agent linked to glucose, most of those compounds have not been approved for the treatment of cancer, and none of those compounds appears to have significant specificity for cancer cells. There remains a need for methods and compositions for treating cancer, including tumors, non-solid cancers, and cancer cells, that are widely applicable in a variety of cancers. The present invention provides such methods, as well as compounds and compositions useful in those methods.

SUMMARY OF THE INVENTION

The present invention provides methods for treating cancer and pre-cancerous cells and tissues, as well as compounds that are conjugates of glucose or an analog or derivative thereof and an anti-cancer agent and compositions for use in the methods of the invention.

In one aspect, the present invention provides methods for treating cancer in a subject, comprising administering to the subject an effective amount of a non-releasable glucose-anti-neoplastic agent conjugate, wherein the glucose portion is a glucose or a derivative or analog thereof, such as 2-deoxyglucose.

In one group of embodiments, the glucose-anti-neoplastic agent conjugate has the formula: Glc-L-Z, wherein Glc is glucose, 2-deoxyglucose, or a 2-deoxyglucose derivative; L is a non-releasable linkage; and Z is an anti-neoplastic agent. Preferred linkages between Glc and L include either an ether or a carbamate linker to the oxygen at the 2 position of glucose and either an alkyl amine, amide, carbamate, urea, or sulfonamide linkage to the nitrogen at the 2 position of glucosamine. Preferred 2-deoxyglucoses and derivatives are D-(+)-2-deoxyglucose and D-(+)-2-amino-2-deoxyglucose. The above method can also be carried out as part of a combination therapy method wherein at least one additional anti-neoplastic agent is administered to the subject either before, during, or after administration of the glucose-anti-neoplastic agent conjugate.

The methods of the invention find broad applicability to the treatment of a number of cancers, due in large part to their ability to treat cancer at the cellular level, including cancers such as lung cancer, breast cancer, prostate cancer, colon cancer, cervical cancer, esophageal cancer, bladder cancer, head and neck cancer, melanoma, low grade non-Hodgkin's Lymphoma, intermediate grade non-Hodgkin's Lymphoma, follicular lymphoma, large cell lymphoma, B-cell lymphoma, T-cell lymphoma, Mantle cell lymphoma, Burkitt's lymphoma, NK cell lymphoma, and acute lymphoblastic lymphoma.

In some embodiments, additional steps can be employed in the present methods, including an initial step of reducing glucose ingestion in a subject prior to administering (and/or during administration of) the glucose-anti-neoplastic agent conjugate. Typically, this can be accomplished by withholding carbohydrate consumption for a period of up to 12–48 hours prior to administration of the conjugate. In another embodiment, the patient is administered an oral hypoglycemic agent prior to or contemporaneously with administration of the conjugate. Suitable oral hypoglycemic agents include but are not limited to metmorphin (Tolbutamide) and sulfonylurea (Glipizide). Also, a patient can be administered a high fat meal prior to administration, as free fatty acids block the uptake of glucose in the heart, and so can be used to prevent normal tissues from up-taking a conjugate of the invention.

In a related aspect, the present invention provides methods for treating pre-cancer cells in a subject, comprising administering to the subject an effective amount of a glucose-anti-neoplastic agent conjugate. In one embodiment, the method is applied to the treatment of benign prostatic hypertrophy.

In another related aspect, the present invention provides a method for enhanced delivery of an anti-neoplastic agent into cancer cells.

BRIEF DESCRIPTION OF THE DRAWINGS

The FIGURE illustrates the uptake of a glucosamine-DOTA/Indium conjugate in Raji lymphoma cells, in the presence and absence of cytochalasin B.

DETAILED DESCRIPTION OF THE INVENTION

The following sections describe the invention in detail, beginning with a list of definitions and a general description of the invention. A description of the embodiments of the invention follows, which is composed of five main parts, labeled A–E, which respectively describe methods of treating cancer generally; methods of treating particular cancers, including lung, ovarian, prostate, and colon cancer, and central nervous system lymphoma and leukemia; administration and formulation of the conjugates of the invention; the conjugates of the invention, including the glucose moiety, the anti-neoplastic agent, the linker, and the site of attachment; and kits useful in the practice of the invention.

Abbreviations and Definitions

As used herein, the term "cancer" in a mammal refers to any of a number of conditions caused by the abnormal, uncontrolled growth of cells. Cells capable of causing cancer, called "cancer cells", possess a number of characteristic properties such as uncontrolled proliferation, immortality, metastatic potential, rapid growth and proliferation rate, and certain morphological features. Often, cancer cells will be in the form of a tumor, but such cells may also exist alone within a mammal, or may be non-tumorigenic, such as leukemia cells. A cancer can be detected in any of a number of ways, including, but not limited to, detecting the presence of a tumor or tumors (for example, by clinical or radiological means), examining cells within a tumor or from another biological sample (for example, from a tissue biopsy), measuring blood markers indicative of cancer (for example, CA125, PAP, PSA, CEA, AFP, HCG, CA 19-9, CA 15-3, CA 27–29, LDH, NSE, and others), detecting a genotype indicative of a cancer (for example, TP53, ATM, and the like). However, a negative result in one or more of the above detection methods does not necessarily indicate the absence of cancer: a patient who has exhibited a complete response to a cancer treatment may still have a cancer, as evidenced by a subsequent relapse.

The term "pre-cancer" in a mammal refers to a change in the cells of a particular organ, for example the lungs, which looks like true cancer but does not attack the body as true cancer does. The term also applies to conditions of cellular hypertrophy, such as benign prostatic hypertrophy. Such changes or conditions can last for many years before cancer develops, giving time for early detection and treatment in accordance with the methods of the present invention.

The terms "anti-neoplastic agent" and "anti-cancer agent" and "chemotherapeutic agent" refer to a compound that prevents, kills, or blocks the growth and spread of cancer cells. The term is inclusive of those agents that are considered alkylating agents, antimetabolites, radionuclides, metal poisons, enzyme inhibitors, and the like.

General

The present invention derives in part from the discovery that certain conjugates of glucose and glucose derivatives, particularly 2-deoxyglucosamine, and anti-neoplastic agents linked via non-releasable linkages experience enhanced uptake in cancer cells relative to non-cancer cells, similar to the enhanced rate of glucose uptake that has been observed for certain cancer cells. Equally important to the therapeutic efficacy of such compounds is that the conjugate compounds of the present invention having such non-releasable linkages are, once phosphorylated by hexokinase at the 6-position of the glucose or glucose-like moiety of the compound, retained in the cancer cells and can exert their anti-neoplastic activity without the requirement of either degradation or elimination of components (as is the case, for example, with the streptozotocin, glufosfamide, and 2-gluSNAP conjugates described in the Background section above). Accordingly, the compounds and compositions provided herein are useful in treating cancer.

The present invention provides methods for the treatment of cancer in which anti-neoplastic agents conjugated to glucose or a derivative thereof such as 2-glucosamine are administered to a subject, and after administration, bind specifically to one or more of the glucose transport proteins on the surface of cancer cells, ultimately being translocated into the cell. Once inside the cell, the conjugates provided herein are, due to the glucose moiety, subject to phosphorylation of the glucose moiety by hexokinase and retained in the cell. Accumulation of these conjugates and/or the action of the cytotoxic moiety within the cancer cell causes death of the cancer cell.

Compositions of the present invention comprise glucose or a derivative thereof such as 2-deoxyglucosamine covalently attached via a non-releasable linkage to an anti-neoplastic agent that, when accumulated within the cancer cell, causes the death of the cancer cell by interaction with the DNA, proteins, or sub-cellular machinery of the cell. The methods employing these conjugates encompass several embodiments.

In some embodiments, the conjugates described herein utilize a glucose molecule that lacks an oxygen atom or hydroxy group at the 2 position and hence are 2-deoxy-D-glucose conjugates. 2-Deoxy-D-Glucose (2-DG) differs from glucose in the replacement of one hydroxy group by a hydrogen atom. The cells of the body recognize 2-DG and certain of its analogs and derivatives in the same way that the cells recognize glucose, until a point in the glycolytic pathway where the structural difference prevents further metabolism. 2-DG and glucose are transported into the cell by the same membrane-bound transporters (glucose transporters, such as the GLUT proteins) that are over-expressed in cancer cells, and they are both metabolized to a 6-phosphate form by hexokinase, an intracellular enzyme. Hexokinase type II is over-expressed in many cancer cells, where it plays a pivotal role in the high glycolytic phenotype of these cells. This over-expression can result from stable gene amplification and up-regulation of the promoter of the gene encoding this enzyme.

Once 2-DG and glucose are transported into the cell and phosphorylated at the 6 position, the metabolic fate of the molecules diverge. Glucose follows several enzymatically driven pathways: (1) incorporation into glycogen, (2) metabolism into the hexose monophosphate shunt, and (3) metabolism to pyruvate further down the glycolytic path. 2-DG-6-phosphate is not subject to metabolism by any of the enzymes responsible for these pathways, despite the slight difference in structure from glucose. The metabolic fate remaining for 2-DG-6-phosphate is to undergo removal of the phosphate mediated by intracellular phosphatases. This enzyme is also expressed differentially in cancer cells relative to normal cells: cancer cells have decreased expression of the needed phosphatase relative to normal cells.

In one embodiment, the present invention provides conjugates of 2-deoxy-D-glucose and certain derivatives and structurally similar analogs thereof that are subject to phosphorylation, as is D-glucose, but are not further metabolized by the glucose metabolic pathways. Due to the markedly enhanced utilization of glucose in cancer cells mediated by increased activity of the proteins mediating these steps, the 2-deoxy-D-glucose and related conjugates are accumulated preferentially in cancer cells compared to normal cells. As will be appreciated upon contemplation of the disclosure hereof, a 2-DG conjugate of the invention is usually prepared from a compound other than 2-DG, which is relatively inert to chemical modification at the 2 position. Thus, a compound falling within the definition of a "Glc" herein is not necessarily the compound used in the synthesis of a conjugate of the invention, and, unless otherwise indicated, "2-DG" simply refers to a glucose-like moiety lacking a hydroxyl or oxygen or ester linkage at the 2 position.

The conjugates of the invention can be used to treat cancer tissue and cancer cells preferentially. The selectivity of the conjugates for preferentially killing cancer cells is provided by the increased transport, relative to non-cancer cells, of the conjugate due to the up-regulation of the glucose transporters (GLUTs) in cancer cells, as well as by, at least in some cancer cells, the up-regulated expression of hexokinase. The efficacy of the conjugates, relative to glucose conjugates of anti-neoplastic agents previously known, is due to one or more of several properties, including (i) the conjugate is itself cytotoxic, requiring no cleavage or release to generate a cytotoxin; (ii) the glucose moiety is linked to the anti-neoplastic agent by a non-releasable linker sufficiently stable to ensure that the conjugate remains in the cell for a sufficient period of time to ensure that the anti-neoplastic agent will exert its effect in the cancer cell, instead of being released from the conjugate and diffusing out of the cell; and (iii) the conjugate is phosphorylated or otherwise sequestered in the cell to which it is transported, thereby preventing its subsequent release from the cell, again ensuring that the conjugate remains in the cell it is targeted to kill. The selective uptake of the glucose-anti-neoplastic agent conjugate by cancer cells allows cancer tissue to be treated with reduced toxicity to the surrounding normal tissue, relative to the toxicity that the surrounding tissue would experience if the anti-neoplastic agent were delivered in an un-conjugated form. Moreover, the use of non-releasable and non-diffusible conjugates allows for the concentration of anti-neoplastic agents to build up in the cancer cells rather than be released and diffuse out of the cells. As a result, the amount of anti-neoplastic agent used to treat the cancer may be increased, allowing more effective treatment of the cancer.

More specifically, in one method of the present invention, an oncologist treats tumor tissue with a glucose-anti-neoplastic agent conjugate using an amount, on a molecule-by-molecule basis, greater than the amount used for treatment with the un-conjugated anti-neoplastic agent, such greater amount having, relative to treatment with the un-conjugated anti-neoplastic agent, decreased toxicity to normal cells, thus allowing a more effective treatment of the tumor tissue and a better outcome for the patient. Conversely, by virtue of the improved targeting of cancer cells, relative to their un-conjugated counterparts, the conjugates of the invention can be administered at lower doses with equal efficacy. In either of these embodiments, the present invention in effect reduces the exposure of normal cells to the toxicity of anti-neoplastic agents, therefore allowing more effective treatment of cancer and tumor tissue.

Additionally, administration of the glucose-anti-neoplastic agent conjugate to a human can be carried out to treat pre-cancer in any organ. For example, an individual who is at high risk for developing breast cancer because of family history can be examined after administration of a fluorescent glucose conjugate to detect pre-cancerous cells (see PCT patent application No. US02/41339, incorporated herein by reference). As another example, an individual suffering from benign prostatic hypertrophy can be administered a conjugate of the invention to treat or otherwise ameliorate the symptoms of this condition. Thus, pre-cancerous tissue can be treated by administering an effective amount of a glucose-anti-neoplastic agent conjugate of the invention.

Descriptions of the Embodiments

The methods, compounds, and compositions of the present invention are useful in the treatment of cancer as primary, single-agent treatment, as well as in treatment in combination with radiation, surgery, other anti-cancer agents, and combinations of such standard therapies. Typically, the methods of the invention involve contacting sites on a subject suspected of being cancer sites with an effective amount of a glucose-anti-neoplastic agent conjugate. Effectiveness of treatment can be monitored, if necessary or desired, using a variety of methods, including, for example, visualization of cancer or pre-cancer cells that have been imaged using PET or CAT scans, MRI, or a by use of fluorescent glucose conjugate.

In most embodiments, the treatment methods of the invention are practiced by a clinician or oncologist to treat a patient with cancer cells and tissue. The methods described herein can be combined with various other methods of cancer treatment, such as surgery or anti-cancer monoclonal antibody therapy, for the most effective treatment of the cancer possible, and further derive advantage from the preferential uptake of the conjugate into cancer cells over normal cells.

A. Methods of Treating Cancer

The present invention provides, in one aspect, methods for treating cancer in a subject, comprising administering to said subject an effective amount of a glucose-anti-neoplastic agent conjugate, preferably one having the formula: Glc-L-Z, wherein Glc is glucose or an analog or derivative thereof, such as 2-deoxy-D-glucose or 2-glucosamine; L is non-releasable linkage; and Z is an anti-neoplastic agent. In some embodiments, Z is an anti-neoplastic agent other than N-nitroso urea, ifosfamide, a nitrosothiol, nitric oxide, and a radioisotope. In some embodiments, L is attached to Glu at a position other than the 1 and 6 positions of Glu. Conjugates useful in the methods of the invention form yet another aspect of the present invention as do pharmaceutical formulations of such compounds.

Administration of the anti-neoplastic conjugates provided herein can be effected by any method that enables delivery of the conjugates to the site of action. In some embodiments, the conjugates come into contact with the cancer cells or tumor tissue via circulation in the bloodstream. To place the conjugates in contact with cancer tissues or cells, suitable methods of administration include oral routes, intraduodenal routes, parenteral injection (including intravenous, subcutaneous, intramuscular, intravascular or infusion), topical, and rectal routes. Depending on the type of cancer being treated and the route of administration, certain methods and conjugates are preferred.

Administration of the anti-neoplastic conjugates provided herein can also be accompanied by additional treatment steps directed at preventing or lessening the uptake of the conjugates by non-cancer cells and tissues. For example, the heart is known to uptake glucose rapidly, but such uptake can be eliminated or lessened by reducing glucose ingestion in a subject prior to administering the glucose-anti-neoplastic agent conjugate. Typically, this can be accomplished by withholding carbohydrate consumption for a period of up to 4, 8, 12, 16, 24, or 48 hours prior to administration of the conjugate. In addition, uptake of a glucose conjugate by heart tissue can be prevented or lessened by the administration of fat, including but not limited to ingestion by the patient of a high-fat meal prior to administration of the conjugate, as free fatty acids block the uptake of glucose in the heart. In similar fashion, uptake of a conjugate of the invention by cells or tissues in the urinary tract, such as bladder cells, can be prevented or lessened by aggressive hydration, diuretics, urinary bladder catherterization, and/or lavage. Such methods of the invention are applicable not only to the novel compounds provided by the present invention but also to previously known compounds that are transported into cells by a glucose transporter, including streptozotocin, 2gluSNAP, glufosfamide, and analogs and derivatives thereof. Such methods can be practiced in conjunction with other methods of the invention for increasing the uptake of a glucose conjugate by cancer cells.

Thus, in another method of the invention, uptake of a glucose or glucose analog-anti-neoplastic agent conjugate by a cancer cell is increased by co-administering a hypoglycemic agent to the subject to be treated. As noted above, this method of the invention can be practiced not only with the novel conjugates of the invention but also with previously known compounds as well, including streptozotocin, 2gluSNAP, glufosfamide, and analogs and derivatives thereof. In one embodiment, the hypoglycemic agent that is co-administered with the conjugate is administered orally. Illustrative orally administered hypoglycemic agents include but are not limited to metmorphin (Tolbutamide) and sulfonylurea (Glipizide). Such treatment can increase the amount of uptake of the conjugate by the cancer cells.

Other methods of the invention for increasing the uptake of a glucose or glucose analog-anti-neoplastic agent conjugate by a cancer cell include co-administering a compound selected from the group consisting of N-hydroxyurea, nitric oxide, or a compound that generates nitric oxide, including but not limited to an organic nitrite and a spermineNONOate. Such compounds stimulate the uptake of glucose and thus can be used to stimulate the uptake of a conjugate of the invention or a previously known glucose conjugate compound by cancer cells.

Thus, the present invention provides methods, compositions, and compounds generally useful in the treatment of cancer. Particular cancers susceptible to treatment in accordance with the invention are discussed in the following section.

B. Treating Particular Cancers

The present invention provides methods for treating particular types of cancer, including but not limited to non-small cell lung cancer, head and neck squamous cancers, prostate cancer, and breast cancer in humans and other mammals in need of such treatment. These methods comprise administering a therapeutically effective amount of a conjugate of the invention or a pharmaceutically acceptable salt thereof either alone or in combination with a therapeutically effective amount of one or more additional anti-cancer compounds. For purposes of illustration and not limitation, methods for treating particular types of cancer are described below.

The methods and compositions of the present invention can be used to treat the most common cancers, including but not limited to bladder cancer, breast cancer, colorectal cancer, endometrial cancer, head and neck cancer, leukemia, lung cancer, lymphoma, melanoma, non-small cell lung cancer, ovarian cancer, and prostate cancer.

The methods and compositions of the present invention can also be used to treat less common cancers, including but not limited to acute lymphocytic leukemia, adult acute myeloid leukemia, adult non-Hodgkin's lymphoma, brain tumors, cervical cancers, childhood cancers, childhood sarcoma, chronic lymphocytic leukemia, chronic myeloid leukemia, esophageal cancer, hairy cell leukemia, kidney cancer, liver cancer (which may be especially susceptible to treatment with conjugates of the invention in which the Glc moiety is D-galactose or 2-deoxy-2-amino-D-galactosamine), multiple myeloma, neuroblastoma, oral cancer, pancreatic cancer, primary central nervous system lymphoma, skin cancer, and small-cell lung cancer. Childhood cancers amenable to treatment by the methods and with the compositions of the present invention include but are not limited to brain stem glioma, cerebellar astrocytoma, cerebral astrocytoma, ependymoma, Ewing's sarcoma and family of tumors, germ cell tumor—extracranial, Hodgkin's disease, ALL, AML, liver cancer, medulloblastoma, neuroblastoma, non-Hodgkin's lymphoma, osteosarcoma, malignant fibrous histiocytoma of bone, retinoblastoma, rhabdomyosarcoma, soft tissue sarcoma, supratentorial primitive neuroectodermal and pineal tumors, unusual childhood cancers, visual pathway and hypothalamic glioma, and Wilms's tumor and other childhood kidney tumors.

The methods and compositions of the present invention can also be used to treat cancers that have originated in or metastasized to the bone, brain, breast, digestive and gastrointestinal systems, endocrine system, eye, genitourinary tract, germ cells, gynecological system, head and neck, hematologic system, blood, lung, respiratory system, thorax, musculoskeletal system, and skin. The methods of the present invention are generally applicable to all cancers but have particularly significant therapeutic benefit in the treatment of solid tumors, which are characterized by extensive regions of hypoxic tissue. Specific illustrative treatment methods of the invention for such tumors are described below.

1. Lung Cancer

Current protocols for the treatment of small cell lung cancer involve the integration of chemotherapy with or without radiotherapy or surgery. Glucose conjugation of the chemotherapeutic agents used to treat various forms of lung cancer enhances their efficacy by enhancing their uptake by the lung cancer cells. A variety of effective combination chemotherapy regimens have been reported for small cell lung cancer, including the combinations consisting of cyclophosphamide, doxorubicin and vincristine (CAV); etoposide and cisplatin (VP-16); and cyclophosphamide, doxorubicin and VP-16 (CAVP-16). Recent results suggest modest survival benefits from combination chemotherapy (etoposide plus cisplatin) treatment of non-small cell lung cancer. Each of the chemotherapeutic agents mentioned above can be conjugated to glucose to provide a conjugate of the invention, according to the methods described herein to enhance their uptake by cancer cells. For example, conjugates of the invention comprising glucose and doxorubicin may be generated in which the 2- or 3-position of glucose is attached to doxorubicin at the 3'-amine (see U.S. Pat. No. 6,177,404, incorporated herein by reference, for illustrative suitable sites of attachment to selected anti-cancer agents).

In one preferred embodiment of the invention, a conjugate of the invention is used to treat non-small-cell lung cancer. Current treatment regiments for non-small-cell lung cancer include without limitation administration of Gemcitabine, Vinorelbine, Paclitaxel, Docetaxel, cisplatin, carboplatin, or Irinotecan as single agents; and administration of Etoposide and cisplatin, Vindesine and cisplatin, Paclitaxel and carboplatin, Gemcitabine and carboplatin, Docetaxel and cisplatin, Vinorelbine and cisplatin, or Irinotecan and cisplatin in combination therapies. See the reference Bunn, 15 Sep. 2002, *J. Clin. Onc.* 20(18s): 23–33, incorporated herein by reference. In accordance with the methods of the present invention, a conjugate of the invention can be co-administered in such therapeutic regimens, or can be used to replace a currently used agent in such a regimen, in which case the anti-neoplastic agent in the conjugate can be the same as or different from the anti-neoplastic agent replaced, or can be administered as a single agent to improve patient outcomes.

2. Ovarian Cancer

The most active drugs in the treatment of ovarian cancer have been alkylating agents or cross-linking agents, including cyclophosphamide, ifosfamide, melphalan, chlorambucil, thiotepa, cisplatin, and carboplatin. Conjugation of such alkylating or cross-linking agents to glucose to provide a conjugate of the invention enhances, relative to the unconjugated agent, uptake by the ovarian cancer cells, therefore allowing more effective and efficient chemotherapy treatment. Current therapy for ovarian cancer includes cisplatin or carboplatin in combination with cyclophosphamide at 3- to 4-week intervals for six to eight cycles. In accordance with the methods of the present invention, a conjugate of the invention can be co-administered in such therapeutic regimens, or can be used to replace a currently used agent in such a regimen, in which case the anti-neoplastic agent in the conjugate can be the same as or different from the anti-neoplastic agent replaced, or can be administered as a single agent to improve patient outcomes.

3. Prostate Cancer

Several comprehensive trials utilizing chemotherapy have been undertaken in late stage prostate cancer following relapse after hormonal treatment. The agents studied most extensively are estramustine phosphate, prednimustine, and cisplatin. Combination chemotherapy is also used to treat prostate cancer, including treatment with estramustine phosphate plus prednimustine and cisplatin, and 5-fluorouracil, melphalan, and hydroxyurea. The methods of the present invention can be applied to generate glucose conjugates of the chemotherapeutic agents used to treat prostate cancer, thereby enhancing their uptake by cancer cells. In accordance with the methods of the present invention, a conjugate of the invention can be co-administered in such therapeutic regimens, or can be used to replace a currently used agent in such a regimen, in which case the anti-neoplastic agent in the conjugate can be the same as or different from the anti-neoplastic agent replaced, or can be administered as a single agent to improve patient outcomes.

4. Colon Cancer

While chemotherapy in patients with advanced colorectal cancer has proven to be of only marginal benefit, 5-fluorouracil is the most effective treatment for this disease. 5-Fluorouracil (5-FU) is useful alone or in combination with other drugs, but is associated with only a 15 to 20 percent likelihood of reducing measurable tumor masses by 50 percent or more. Therefore, it would be beneficial to increase the efficacy of 5-fluorouracil by conjugating it to glucose, as described herein, thus enhancing its uptake by cancer cells. Additionally, conjugates with camptothecin and camptothecin analogs are particularly useful for the treatment of colon cancer. In one embodiment of the invention, the 5-FU conjugate has a linker that hydrolyzes and releases 5-FU in an active form. Since 5-FU activity requires hydrolysis, the linker is preferably non-releasable during transport and releasable in the target cell. In this embodiment, the linker is stable to hydrolysis in the blood, if administered i.v., and/or stomach, if administered orally, but hydrolyzes in the cell, after a time sufficient to allow uptake of the conjugate by cancer cells.

C. Administration and Formulation

The amount of the conjugate administered will be dependent on the subject being treated, the type and severity of the cancer, localization of the cancer, the rate of administration, the disposition of the conjugate (e.g., solubility and cytotoxicity) and the discretion of the prescribing physician. However, an effective dosage is typically in the range of about 0.001 to about 100 mg per kg body weight, preferably about 1 to about 35 mg/kg/day, in single or divided doses. For a 70 kg human, this would amount to about 0.05 to about 7 g/day, preferably about 0.7 to about 2.5 g/day. In some instances, dosage levels below the lower limit of the aforesaid range may be more than adequate, while in other cases still larger doses may be employed without causing any harmful side effect, particularly if such larger doses are first divided into several small doses for administration throughout the day.

The anti-neoplastic conjugate composition may, for example, be in a form suitable for oral administration as a tablet capsule, pill powder, sustained release formulations, solution, suspension, for parenteral injection as a sterile solution, suspension or emulsion, for topical administration as an ointment or cream, or for rectal administration as a suppository. The anti-neoplastic conjugate composition may be in unit dosage forms suitable for single administration of precise dosages and will typically include a conventional pharmaceutical carrier or excipient.

Exemplary parenteral administration forms include solutions or suspensions of the conjugate in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the imaging conjugate therein may be combined with various sweetening or flavoring agents, coloring matters or dyes and, if desired, emulsifying agents or suspending agents, together with diluents such as water, ethanol, propylene glycol, glycerin, or combinations thereof.

Topical formulations of the conjugates of the invention can be used to treat skin cancer. Such formulations can be conveniently prepared using oil-water emulsions and liposomes and may optionally include one or more additional anti-cancer agents.

The present invention also provides slow release forms of the conjugates of the present invention in which an acid labile polyethylene glycol (PEG) moiety is attached to the conjugate, preferably at the hydroxyl groups at the 4 and 6 positions. Such a slow release form can be readily synthesized by first treating PEG with Des Martin periodinane and reacting the resulting aldehyde with a conjugate of the invention. For a 2-glucosamine conjugate of the invention, the resulting compound has the structure:

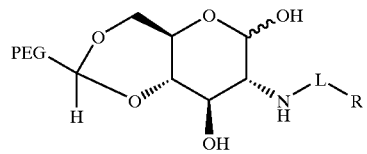

where L is the linker, and R is the anti-neoplastic agent.

Methods of preparing various pharmaceutical compositions with a specific amount of active agent are known, or will be apparent, to those skilled in this art, and can be applied to the conjugates of the invention in view of this disclosure. For examples of suitable formulations and processes, see Remington's Pharmaceutical Sciences, Mack Publishing Company, Easter, Pa., 15$^{th}$ Edition (1975).

D. Glucose-Anti-Neoplastic Agent Conjugates

As noted above, the conjugates employed in the methods herein are yet another aspect of the present invention. These conjugates are represented by the formula: Glc-L-Z, wherein Glc is glucose, preferably an analog or derivative thereof, such as 2-deoxy-D-glucose or a 2-DG derivative such as 2-glucosamine; L is a non-releasable linkage; and Z is an anti-neoplastic agent.

1. Glucose, 2-Deoxy-D-Glucose, and 2-DG-Derivatives

Many of the glucose, 2-DG, and 2-DG derivative components of the conjugates described herein are generally derived from compounds that are commercially available or can be prepared from commercially available material. The glucose derivatives of the conjugates of the invention include derivatives having ($C_1$–$C_{12}$)acyl groups or ($C_1$–$C_{12}$) alkyl groups attached via —O— or —NH— groups at the 3- and 4-positions of the glucose molecule as noted in the formulae below. Additionally, the glucose derivative will, in some embodiments, have a solubility or partitioning effector component attached at the 1-, 3- or 4-positions.

In some embodiments of the conjugates of the invention, the Glc moiety is a glucose analog, such analogs including glucose derivatives such as D-(+)-2-deoxyglucose, D-(+)-2-amino-2-deoxy-glucose or N-acetyl D-(+)-2-amino-2-deoxyglucose; D-mannose and mannose derivatives; D-gulose and D-gulose derivatives, including but not limited to D-3-amino-3-deoxy-gulose and D-2-amino-2-deoxy-gulose; and D-galactose and galactose derivatives including but not limited to D-2-deoxy-D-galactose, D-4-amino-4-deoxy-galactose and D-2-amino-2-deoxy-galactose. Thus, the Glc moiety can differ from D-glucose or a derivative such as 2-DG and 2-glucosamine in that it is an epimer thereof. In addition, the Glc moiety can be a fluorinated derivative of any of the foregoing compounds. Moreover, the oxygen in the ring of any of the foregoing compounds can be substituted with an isostere selected from the group consisting of S, sulfone, and the like. For example, Glc can be 5-thio-D-glucose or a derivative thereof.

2. Linking Groups

The anti-neoplastic agents used herein can be attached to the glucose or glucose derivative using essentially any linkage chemistry that is compatible with both the anti-neoplastic agent and the glucose or glucose derivative portions, but provides a non-releasable attachment between those two components. As used herein, the term "non-releasable" refers to a linkage that is less than 50% cleaved under physiologic conditions in a period of about 0.5 to 2 hours, which allows sufficient time for uptake of the conjugate by cancer cells, more preferably (for anti-neoplastic agents that are still active when linked to the linker) less than 40% cleaved, and still more preferably, less than 20%, 10% or 5% cleaved. Evaluation of the stability of such linkage can be made by one of skill in the art using, for example, a model system having a suitable pH and/or cells or components of lysed cells.

In some embodiments, the anti-neoplastic agent can be attached directly to glucose or a glucose derivative using, for example, an available functional group on the anti-neoplastic agent or an isothiocyanate prepared from a particular agent (e.g., an agent having a free amino group that can be converted to an isothiocyanate group) and a suitably protected glucose or a glucose derivative (e.g., tetra O-acetyl-2-deoxy-2-aminoglucose) to form a desired conjugate. In these embodiments, L simply represents a bond, or in the case of isothiocyanate, a thiocarbonyl group. As noted above, a number of protected glucose compounds or derivatives are commercially available, or can be prepared according to well-established methods. In many instances, the glucose moiety having "n" hydroxy or amino groups, will have "n-1" protecting groups, thereby leaving one available reactive functional group as an attachment site for either the anti-neoplastic agent or a linking group. Additionally, the unprotected functional group will be at a known location on the glucose or glucose derivative to prepare conjugates of a desired structure.

A linking group is used to attach the anti-neoplastic agent covalently to the glucose or glucose derivative. The terms "linker" and "linking group" refer to a moiety that connects the glucose or glucose derivative portion and anti-neoplastic agent portion of the conjugate to one another. In such embodiments, any of the commercially available bifunctional linking groups, preferably, heterobifunctional linking groups (see Pierce Catalog), can be used. Alternatively, one of skill in the art can construct a linking group having two or more reactive functional groups to attach the anti-neoplastic agent and the glucose moiety (e.g., heterobifunctional or homobifunctional). In some embodiments, either a plurality of glucose moieties or a plurality of anti-neoplastic agents or both are attached to a multifunctional linking group to provide a conjugate of the invention Typically a linker or linking group has functional groups that are used to interact with and form covalent bonds with functional groups in the components (e.g., anti-neoplastic agents and glucose or glucose derivatives) of the conjugates described and used herein. Examples of functional groups on the linking groups (prior to interaction with other components) include —$NH_2$, —$NHNH_2$, —$ONH_2$, —NHC=(O)$NHNH_2$, —OH, —$CO_2H$, and —SH. One of skill in the art will understand that each of these functional groups can form a covalent linkage to a suitable functional group on the 2-DG portion or the anti-neoplastic agent portion. For example, amino, hydroxy and hydrazino groups can each form a covalent bond with a reactive carboxyl group (e.g., a carboxylic acid chloride or activated ester such as an N-hydroxysuccinimide ester (NHS)), although the ester formed by linking a hydroxyl to a reactive carboxyl group can be cleaved by serum esterases and so may not be preferred in some instances. Other suitable bond forming groups are well-known in the literature. Moreover, the linking group can include linear or acyclic portions, cyclic portions, aromatic rings or combinations thereof. More specifically, the linking group L will typically have from 3 to 100 main chain atoms other than hydrogen atoms, selected from C, N, O, S, P and Si, and may be acyclic. The linking groups are sufficiently robust so that they are stable to reaction conditions used in conjugate assembly, the protection/deprotection chemistries used to prepare the conjugates, illustrative embodiments of which described in more detail below. In related embodiments, a plurality of glucose moieties can be attached to a multifunctional linking group to facilitate uptake of the anti-neoplastic agent. Illustrative linkers and synthetic chemistries are described in more detail below.

The preferred connections between the linker and the glucose or glucose derivative include connection via the oxygen at the 2 position of glucose as an ether or carbamate and connection via the nitrogen at the 2 position of glucosamine as an alkyl amine, amide, carbamate, urea, or sulfonamide. The preferred connections between the linker and the anti-neoplastic agent include connections that do not render the anti-neoplastic agent inactive and connections that are relatively stable in the serum and, for orally administered conjugates, stomach.

Other linking groups useful in the conjugates of the invention are described in U.S. Pat. Nos. 5,512,667; 5,451,463; and 5,141,813. In addition, U.S. Pat. Nos. 5,696,251; 5,585,422; and 6,031,091 describe certain tetrafunctional linking groups useful in the practice of the present invention, either to prepare monomeric conjugates (in which one glucose-like moiety is linked to one anti-neoplastic agent) or to prepare multimeric compositions in which, for example and without limitation, two anti-neoplastic agents are present in the conjugate.

Functional groups on linkers useful in preparing conjugates of the present invention include primary and secondary nitrogen, OH, and —SH. As discussed herein, a preferred deoxyglucose moiety for forming the conjugates of the present invention is D-glucosamine as the hydrochloride salt. This compound has an amino group that provides a chemical handle for conjugations. Anti-neoplastic agents can be conjugated directly to this amino group via alkyl, amide, or sulfonamide linkages, for example. Alternatively, a linker or spacer can separate the anti-neoplastic agent and the glucosamine. The glucosamine is then not sterically impacted by the anti-neoplastic agent and is free to act like glucose in terms of uptake via the glucose transport system and phosphorylation via the hexokinase enzymes, and the action of the anti-neoplastic agent is not hindered by the glucosamine.

Optimal linkers are oligomers of ethylene glycol or straight alkyl chains or mixtures thereof. These linkers are attached to the glucosamine amine via either an alkyl or amide connection. The anti-neoplastic agent is attached to the other end via an amide, sulfonamide, or ether connection. The optimum length of the linker is from 1 to 16 atoms. Illustrative synthetic schemes for forming such conjugates of the invention are discussed below for several preferred linkers of the invention.

An illustrative linker of the invention is derived from N-t-boc-amido-PEG4-acid (available from, for example, Quantabiodesign, Inc., product no. 10220). This linker can be coupled to glucosamine and an anti-neoplastic agent by a reaction scheme in which one first prepares the N-hydroxysuccinimide (NHS) ester of the linker in a reaction mixture containing the N-t-boc-amido-PEG4-acid, one equivalent of 1-(3-dimethylamino)-3-ethylcarbodiimide HCL, and 2 equivalents of NHS in DMF solvent. The resulting NHS-linker is then reacted with one equivalent of the hydrochloride salt of glucosamine and one equivalent of triethylamine in DMF solvent to link the glucosamine to the linker. This product is washed with trifluoroacetic acid, evaporated, and reacted with triethylamine in DMF solvent with an anti-neoplastic agent as a succinimidyl ester to yield a glucosamine-anti-neoplastic agent conjugate of the invention.

The length of the linker arm can be varied as provided by the synthetic methods of the invention. For example, in the case of the amide connections, one can use the derivatives shown below in place of N-t-boc-amido-PEG4-acid.

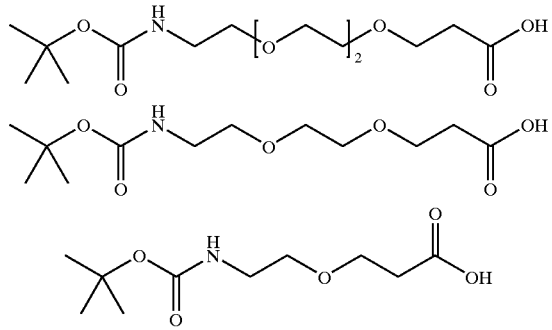

-continued

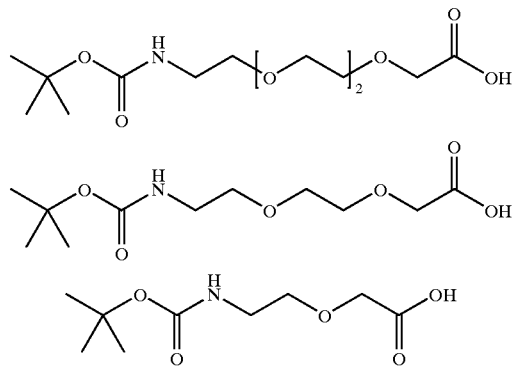

The t-BOC-protected amino acids can be derived from the corresponding amino acid and BOC-ON (commercially available from Aldrich Chemical, product no. 19,337-2). The amino acids in turn can be obtained from published procedures in the chemical literature. One can prepare a glucosamine-anti-neoplastic agent conjugate of the invention using such linkers by the following illustrative synthetic scheme. The N-t-BOC-amido-PEG4-alcohol (commercially available from Quantabiodesign, Inc., product No. 10250) is reacted with 1 equivalent Dess-Martin periodinane. The resulting compound is reacted with three equivalents of fully protected (with acyl protecting groups) glucosamine, which can be made in accordance with the procedure set forth in PCT patent publication No. 99/20316, incorporated herein by reference, and three equivalents of sodium triacetoxy borohydride in THF solvent. The resulting compound is dissolved in sodium methoxide in methanol, extracted with trifluoroacetic acid, and evaporated to dryness. Then, the compound is dissolved in triethylamine in DMF and reacted with 0.5 equivalents of an anti-neoplastic agent as the NHS ester to form a conjugate of the invention.

Again, the length of the linker arm can be varied. For example, in the case of the alkyl connection, one can use the derivatives shown below in place of N-t-BOC-amido-PEG4-alcohol (Quantabiodesign Inc product number 10250).

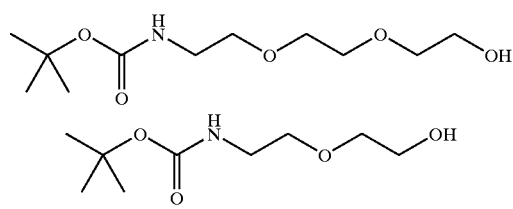

These t-BOC-protected amino alcohols can be derived, for example, from the corresponding amino alcohols and BOC-ON. The amino alcohols in turn can be obtained from published procedures in the chemical literature.

Alternatively, the starting amino acids and alcohols for the conjugates can comprise all alkyl chains, as shown below. The amino acids and alcohols are available commercially (Aldrich Chemical) and can be derivatized with BOC-ON to produce the reagents shown below.

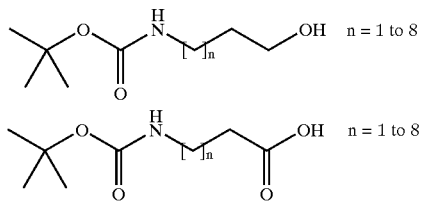

In one embodiment of the conjugates of the invention, L is a bond such that the anti-neoplastic agent is directly attached to the glucose or glucose derivative, such as glucosamine. Typically, this attachment is accomplished via coupling of a functional group on the anti-neoplastic agent with a compatible (e.g., linkage-forming) functional group on the glucose derivative. In certain preferred embodiments, the anti-neoplastic agent has an isocyanate, isothiocyanate or carboxylic acid functional group that is used to attach that agent to a hydroxy or amino group present on the Glc moiety to form a carbamate, thiocarbamate, urea or thiourea linkage between the components.

In another group of embodiments, L is a linking group that can be essentially any of the linking groups discussed above or another linking group generally known to those of skill in the art. The linking group in this aspect of the invention typically has from 1 to 100 main chain atoms other than hydrogen atoms, selected from C, N, O, S, P and Si, and can be cyclic, acyclic, aromatic or a combination thereof. Additionally, the linking groups are sufficiently robust so that they are stable not only to reaction conditions used in conjugate assembly, but are also stable to conditions within a cancer cell. More particularly, the linking group is one that is stable to hydrolytic and proteolytic conditions that are typically found in a cancer cell (e.g., exhibits a $t_{1/2}$ for hydrolysis or cleavage of the linkage of at least about 0.5–4 hours at ambient temperatures in a cancer cellular milieu). Preferred linking groups include both homo- and hetero-bifunctional linking groups, as are commercially available or readily prepared according to known methods.

3. Anti-Neoplastic Agents

A variety of anti-neoplastic agents are useful in preparing the conjugates of the present invention, including chemotherapeutic agents, radioisotopic agents, and chelating agents that, in some embodiments, carry a radioisotope or other metal agent or, in other embodiments, bind to an essential metal ion in the cancer cell. To facilitate uptake of the conjugate through a glucose transporter, however, the anti-neoplastic agent is, in a preferred embodiment, a relatively small molecule, for example, a molecule having a molecular weight less than 1,000 daltons, preferably less than 800 daltons, and most preferably less than 500 daltons. In further preferred embodiments, the anti-neoplastic agent and the linking group together have a molecular weight of from about 200 to about 2000 daltons, or 250 to about 1500 daltons, or 300 to about 1250 daltons, or 400 to about 1000 daltons.

More particularly, the attached anti-neoplastic agent is preferably an agent that kills dividing cells, arrests cell division, or prevents metastasis. In the case of toxic molecules, the anti-neoplastic agent can include radionuclides and heavy metal poisons (often contained in a chelating agent), known chemotherapeutic agents, or other molecules known to interact with DNA, RNA or proteins in such a way as to kill the exposed cell.

Suitable radionuclides include, for example, Yttrium-90, Iodine-125, Iodine-131, and Phosphate-32. Preferred anti-neoplastic agents comprising a radionuclide include iodoaryl groups bearing an Iodine-131. Other preferred anti-neoplastic agents include hydroxyurea and other ribonucleotide reductase inhibitors based on iron chelation such as Triapine (3-aminopyridine-2-carboxaldehyde thiosemicarabazone) and 5-HP (5-hydroxypyridine-2-carboxaldehyde thiosemicarbazone).

Less preferred anti-neoplastic agents include camptothecin and its various analogs, carboplat and analogs, DOTA and other radiometal ion chelators, methotrexate and analogs, mitoxantrone and related anthraquinone structures, small protein kinase inhibitors, dacarbazine or procarbazine and mitomycin.

Least preferred anti-neoplastic agents, because of the requirement of conjugate cleavage for activity when these anti-neoplastic agents are employed, are 6-mercaptopurine, 6-thioguanine, cytarabine, 5-fluorouracil, porfiromycin, gemcitabine, fludarabine, pentostatin, melphalan, CCNU, BCNU, cyclophosphamide, and arsenic trioxide.

Least preferred anti-neoplastic agents, because of their large size, include adriamycin, daunomycin, bleomycin, dactinomycin, vincristine, vinblastine, vinorelbine, etoposide, teneposide, taxanes, carminomycin, podophyllotoxin, colchicine, leurosidine, vindesine, dactinomycin, prednisone, vinleurosine, and estramustine.

Selection of other suitable anti-neoplastic agents will take into consideration certain physical and chemical properties such as cytotoxicity, stability, and non-specific binding behavior. Some agents are not currently in use as chemotherapeutic agents and can be rendered useful by the preferential targeting by glucose or a glucose derivative such as 2-DG or glucosamine, including but not limited to trifluoracetate and cyanide. Additionally, one skilled in the art can make chemical modifications to the desired anti-neoplastic agent to make reactions of the agent more convenient for the purposes of forming conjugates of the invention.

In accordance with the methods of the invention, a conjugate of the invention can be co-administered in combination with other anti-cancer and anti-neoplastic agents. When employed in combination with one of these agents, the dosages of the additional agent are either the standard dosages employed for those agents or are adjusted downward or upward from levels employed when that agent is used alone. Thus, the administration of a conjugate in accordance with the methods of the invention can allow the physician to treat cancer with existing drugs, but at a lower concentration or dose than is currently used, thus ameliorating the toxic side effects of such drugs, or at a higher concentration, due to the fact that the conjugate is less toxic than its un-conjugated counterpart. The determination of the exact dosages for a given patient varies, dependent upon a number of factors including the drug combination employed, the particular disease being treated, and the condition and prior history of the patient, but is within the skill of the ordinarily skilled artisan in view of the teachings herein.

Specific dose regimens for known and approved anti-neoplastic agents are given, for example, in the product descriptions found in the current edition of the Physician's Desk Reference, Medical Economics Company, Inc., Oradell, N.J. Illustrative dosage regimens for certain anti-cancer drugs are also provided below. Those of skill in the art will recognize that many of the known anti-cancer drugs discussed herein are routinely used in combination with other drugs. In accordance with the methods of the present invention, a conjugate of the invention can be co-administered in such multiple drug treatment regimens, either in addition to the agents used or in replacement of one or more of such agents, including, in the latter embodiment, replacement of its un-conjugated counterpart.

FDA-approved cancer drugs can be classified generally as alkylators, anthracyclines, antibiotics, aromatase inhibitors, biphosphonates, cyclo-oxygenase inhibitors, estrogen receptor modulators, folate antagonists, inorganic aresenates, microtubule inhibitors, modifiers, nitrosoureas, nucleoside analogs, osteoclast inhibitors, platinum containing compounds, retinoids, topoisomerase 1 inhibitors, topoisomerase 2 inhibitors, and tyrosine kinase inhibitors. In accordance with the methods of the present invention, a conjugate of the invention can be prepared using, or can be co-administered with, any anti-cancer drug from any of these classes and can be administered prior to or after treatment with any such drug.

Alkylators useful in the practice of the present invention include but are not limited to busulfan (Myleran, Busulfex), chlorambucil (Leukeran), cyclophosphamide (Cytoxan, Neosar), melphalan, L-PAM (Alkeran), dacarbazine (DTIC-Dome), and temozolamide (Temodar). In accordance with the methods of the present invention, glucose or 2-DG or a derivative thereof such as glucosamine is conjugated to, or a conjugate of the invention is co-administered with, an alkylator to treat cancer. In one embodiment, the cancer is chronic myelogenous leukemia, multiple myeloma, or anaplastic astrocytoma. As one example, the compound 2-bis[(2-Chloroethyl)amino]tetrahydro-2H-1,3,2-oxazaphosphorine, 2-oxide, also commonly known as cyclophosphamide, is an alkylator used in the treatment of Stages III and IV malignant lymphomas, multiple myeloma, leukemia, mycosis fungoides, neuroblastoma, ovarian adenocarcinoma, retinoblastoma, and carcinoma of the breast. Cyclophosphamide is administered for induction therapy in doses of 1500–1800 mg/m$^2$ that are administered intravenously in divided doses over a period of three to five days; for maintenance therapy, 350–550 mg/m$^2$ are administered every 7–10 days, or 110–185 mg/m$^2$ are administered intravenously twice weekly. In accordance with the methods of the invention, a conjugate of the invention is co-administered with cyclosphosphamide administered at such doses.

Anthracyclines useful in the practice of the present invention include but are not limited to doxorubicin (Adriamycin, Doxil, Rubex), mitoxantrone (Novantrone), idarubicin (Idamycin), valrubicin (Valstar), and epirubicin (Ellence). In accordance with the methods of the present invention, glucose or 2-DG or a derivative thereof such as glucosamine is conjugated to, or a conjugate of the invention is co-administered with, an anthracycline to treat cancer. In one embodiment, the cancer is acute nonlymphocytic leukemia, Kaposi's sarcoma, prostate cancer, bladder cancer, metastatic carcinoma of the ovary, and breast cancer. As one example the compound (8S,10S)-10-[(3-Amino-2,3,6-trideoxy-α-L-lyxo-hexopyranosyl)oxy]-8-glycoloyl-7,8,9,10-tetrahydro-6,8,11-trihydroxy-1-methoxy-5,12-naphthacenedione, more commonly known as doxorubicin, is a cytotoxic anthracycline antibiotic isolated from cultures of *Streptomyces peucetius* var. *caesius*. Doxorubicin has been used successfully to produce regression in disseminated neoplastic conditions such as acute lymphoblastic leukemia, acute myeloblastic leukemia, Wilm's tumor, neuroblastoma, soft tissue and bone sarcomas, breast carcinoma, ovarian carcinoma, transitional cell bladder carcinoma, thyroid carcinoma, lymphomas of both Hodgkin and non-Hodgkin types, bronchogenic carcinoma, and gastric carcinoma. Doxorubicin is typically administered in a dose in the range of 60–75 mg/m$^2$ as a single intravenous injection administered at 21-day intervals; weekly intravenous injection at doses of 20 mg/m$^2$; or 30 mg/m$^2$ doses on each of three successive days repeated every four weeks. In accordance with the methods of the invention, a conjugate of the invention is co-administered with doxorubicin administered at such doses.

Antibiotics useful in the practice of the present invention include but are not limited to dactinomycin, actinomycin D (Cosmegen), bleomycin (Blenoxane), and daunorubicin, daunomycin (Cerubidine, DanuoXome). In accordance with the methods of the present invention, glucose or 2-DG or a derivative thereof such as glucosamine is conjugated to, or a conjugate of the invention is co-administered with, an antibiotic to treat cancer. In one embodiment, the cancer is acute lymphocytic leukemia, other leukemias, and Kaposi's sarcoma.

Aromatase inhibitors useful in the practice of the present invention include but are not limited to anastrozole (Arimidex) and letroazole (Femara). In accordance with the methods of the present invention, glucose or 2-DG or a derivative thereof such as glucosamine is conjugated to, or a conjugate of the invention is co-administered with, an aromatase inhibitor to treat cancer. In one embodiment, the cancer is breast cancer.

Biphosphonate inhibitors useful in the practice of the present invention include but are not limited to zoledronate (Zometa). In accordance with the methods of the present invention, glucose or 2-DG or a derivative thereof such as glucosamine is conjugated to, or a conjugate of the invention is co-administered with, a biphosphonate inhibitor to treat cancer. In one embodiment, the cancer is multiple myeloma, bone metastases from solid tumors, or prostate cancer.

Cyclo-oxygenase inhibitors useful in the practice of the present invention include but are not limited to celecoxib (Celebrex). In accordance with the methods of the present invention, glucose or 2-DG or a derivative thereof such as glucosamine is conjugated to, or a conjugate of the invention is co-administered with, a cyclo-oxygenase inhibitor to treat cancer. In one embodiment, the cancer is colon cancer or a pre-cancerous condition known as familial adenomatous polyposis.

Estrogen receptor modulators useful in the practice of the present invention include but are not limited to tamoxifen (Nolvadex) and fulvestrant (Faslodex). In accordance with the methods of the present invention, glucose or 2-DG or a derivative thereof such as glucosamine is conjugated to, or a conjugate of the invention is co-administered with, an estrogen receptor modulator to treat cancer. In one embodiment, the cancer is breast cancer or the treatment is administered to prevent the occurrence or reoccurrence of breast cancer.

Folate antagonists useful in the practice of the present invention include but are not limited to methotrexate and tremetrexate. In accordance with the methods of the present invention, glucose or 2-DG or a derivative thereof such as glucosamine is conjugated to, or a conjugate of the invention is co-administered with, a folate antagonist to treat cancer. In one embodiment, the cancer is osteosarcoma. Antifolate drugs have been used in cancer chemotherapy for over thirty years. As one example, the compound N-[4-[[(2,4-diamino-6-pteridinyl)methyl methylamino]benzoyl]-L-glutamic acid, commonly known as methotrexate, is an antifolate drug that has been used in the treatment of gestational choriocarcinoma and in the treatment of patients with chorioadenoma destruens and hydatiform mole. It is also useful in the treatment of advanced stages of malignant lymphoma and in the treatment of advanced cases of mycosis fungoides. 5-Methyl-6-[[(3,4,5-trimethoxyphenyl)-amino]methyl]-2,4-quinazolinediamine is another antifolate drug and is commonly known as trimetrexate. Methotrexate is administered as follows. For choriocarcinoma, intramuscular injections of doses of 15 to 30 mg daily for a five-day course, such courses repeated as needed with rest period of one or more weeks interposed between courses of therapy. For leukemias, twice weekly intramuscular injections in doses of 30 mg/m$^2$. For mycosis fungoides, weekly intramuscular injections of doses of 50 mg or, alternatively, of 25 mg twice weekly. In accordance with the methods of the invention, a conjugate of the invention is co-administered with methotrexate administered at such doses.

Inorganic arsenates useful in the practice of the present invention include but are not limited to arsenic trioxide (Trisenox). In accordance with the methods of the present invention, glucose or 2-DG or a derivative thereof such as glucosamine is conjugated to, or a conjugate of the invention is co-administered with, an inorganic arsenate to treat cancer. In one embodiment, the cancer is refractory APL.

Microtubule "inhibitors," which may inhibit either microtubule assembly or disassembly, useful in the practice of the present invention include but are not limited to vincristine (Oncovin), vinblastine (Velban), paclitaxel (Taxol, Paxene), vinorelbine (Navelbine), docetaxel (Taxotere), epothilone B or D or a derivative of either, and discodermolide or its derivatives. In accordance with the methods of the present invention, glucose or 2-DG or a derivative thereof such as glucosamine is conjugated to, or a conjugate of the invention is co-administered with, a microtubule inhibitor to treat cancer. In one embodiment, the cancer is ovarian cancer, breast cancer, non-small cell lung cancer, Kaposi's sarcoma, and metastatic cancer of breast or ovary origin. As one example, the compound 22-oxo-vincaleukoblastine, also commonly known as vincristine, is an alkaloid obtained from the common periwinkle plant (*Vinca rosea*, Linn.) and is useful in the treatment of acute leukemia. It has also been shown to be useful in combination with other oncolytic agents in the treatment of Hodgkin's disease, lymphosarcoma, reticulum-cell sarcoma, rhabdomyosarcoma, neuroblastoma, and Wilm's tumor. Vincristine is administered in weekly intravenous doses of 2 mg/m$^2$ for children and 1.4 mg/m$^2$ for adults. In accordance with the methods of the invention, a conjugate of the invention is co-administered with vincristine administered at such doses.

Modifiers useful in the practice of the present invention include but are not limited to Leucovorin (Wellcovorin), which is used with other drugs such as 5-fluorouracil to treat colorectal cancer. In accordance with the methods of the present invention a conjugate of the invention is co-administered with a modifier and optionally another anti-cancer agent to treat cancer. In one embodiment, the cancer is colon cancer. In one embodiment, the modifier is a compound that increases the ability of a cell to uptake glucose, including but not limited to the compound N-hydroxyurea.

Nitrosoureas useful in the practice of the present invention include but are not limited to procarbazine (Matulane), lomustine, CCNU (CeeBU), carmustine (BCNU, BiCNU, Gliadel Wafer), and estramustine (Emcyt). In accordance with the methods of the present invention, glucose or 2-DG or a derivative thereof such as glucosamine is conjugated to, or a conjugate of the invention is co-administered with, a nitrosourea to treat cancer. In one embodiment, the cancer is prostate cancer or glioblastoma, including recurrent glioblastoma multiforme.

Nucleoside analogs useful in the practice of the present invention include but are not limited to mercaptopurine, 6-MP (Purinethol), fluorouracil, 5-FU (Adrucil), thioguanine, 6-TG (Thioguanine), hydroxyurea (Hydrea), cytarabine (Cytosar-U, DepoCyt), floxuridine (FUDR), fludarabine (Fludara), pentostatin (Nipent), cladribine (Leustatin, 2-CdA), gemcitabine (Gemzar), and capecitabine (Xeloda). In accordance with the methods of the present invention, glucose or 2-DG or a derivative thereof such as glucosamine is conjugated to, or a conjugate of the invention is co-administered with, a nucleoside analog to treat cancer. In one embodiment, the cancer is B-cell lymphocytic leukemia (CLL), hairy cell leukemia, adenocarcinoma of the pancreas, metastatic breast cancer, non-small cell lung cancer, and metastatic colorectal carcinoma. Unlike the anti-neoplastic agents in many of the conjugates of the invention, the nucleoside analogs may require release from the conjugate to be active. If this is the case for a particular nucleoside analog or other anti-neoplastic agent, then the linker and linkage is selected such that the linker is released from the anti-neoplastic after a period of time sufficient for the conjugate to be uptaken by the cancer cell.

As one example, the compound 5-Fluoro-2,4(1H,3H)-pyrimidinedione, also commonly known as 5-fluorouracil, is an antimetabolite nucleoside analog effective in the palliative management of carcinoma of the colon, rectum, breast, stomach, and pancreas in patients who are considered incurable by surgical or other means. 5-Fluorouracil is administered in initial therapy in doses of 12 mg/m$^2$ given intravenously once daily for 4 successive days with the daily dose not exceeding 800 mg. If no toxicity is observed at any time during the course of the therapy, 6 mg/kg are given intravenously on the 6th, 8th, 10th, and 12th days. No therapy is given on the 5th, 7th, 9th, or 11th days. In poor risk patients or those who are not in an adequate nutritional state, a daily dose of 6 mg/kg is administered for three days, with the daily dose not exceeding 400 mg. If no toxicity is observed at any time during the treatment, 3 mg/kg may be given on the 5th, 7th, and 9th days. No therapy is given on the 4th, 6th, or 8th days. A sequence of injections on either schedule constitutes a course of therapy. In accordance with the methods of the invention, a conjugate of the invention is co-administered with 5-FU administered at such doses.

As another example, the compound 2-amino-1,7-dihydro-6H-purine-6-thione, also commonly known as 6-thioguanine, is a nucleoside analog effective in the therapy of acute non-pymphocytic leukemias. 6-Thioguanine is orally administered in doses of about 2 mg/kg of body weight per day. The total daily dose may be given at one time. If after four weeks of dosage at this level there is no improvement, the dosage may be increased to 3 mg/kg/day. In accordance with the methods of the invention, a conjugate of the invention is co-administered with 6-TG administered at such doses.

Osteoclast inhibitors useful in the practice of the present invention include but are not limited to pamidronate (Aredia). In accordance with the methods of the present invention, glucose or 2-DG or a derivative thereof such as glucosamine is conjugated to, or a conjugate of the invention is co-administered with, an osteoclast inhibitor to treat cancer. In one embodiment, the cancer is osteolytic bone metastases of breast cancer, and one or more additional anti-cancer agents are also co-administered with a conjugate of the invention.

Platinum compounds useful in the practice of the present invention include but are not limited to cisplatin (Platinol) and carboplatin (Paraplatin). In accordance with the methods of the present invention, glucose or 2-DG or a derivative thereof such as glucosamine is conjugated to, or a conjugate of the invention is co-administered with, a platinum compound to treat cancer. In one embodiment, the cancer is metastatic testicular cancer, metastatic ovarian cancer, ovarian carcinoma, and transitional cell bladder cancer. As one example, the compound cis-Diaminedichloroplatinum (II), commonly known as cisplatin, is useful in the palliative treatment of metastatic testicular and ovarian tumors, and for the treatment of transitional cell bladder cancer which is not amenable to surgery or radiotherapy. Cisplatin, when used for advanced bladder cancer, is administered in intravenous injections of doses of 50–70 mg/m$^2$ once every three to four weeks. In accordance with the methods of the present invention, a conjugate of the invention is co-administered with cisplatin administered at these doses. One or more additional anti-cancer agents can be co-administered with the platinum compound and a conjugate of the invention. As one example, Platinol, Blenoxane, and Velbam may be co-administered with a conjugate of the invention. As another example, Platinol and Adriamycin may be co-administered with a conjugate of the invention.

Retinoids useful in the practice of the present invention include but are not limited to tretinoin, ATRA (Vesanoid), alitretinoin (Panretin), and bexarotene (Targretin). In accordance with the methods of the present invention, glucose or 2-DG or a derivative thereof such as glucosamine is conjugated to, or a conjugate of the invention is co-administered with, a retinoid to treat cancer. In one embodiment, the cancer is acute promyelocytic leukemia (APL), Kaposi's sarcoma, or T-cell lymphoma.

Topoisomerase 1 inhibitors useful in the practice of the present invention include but are not limited to topotecan (Hycamtin) and irinotecan (Camptostar). In accordance with the methods of the present invention, glucose or 2-DG or a derivative thereof such as glucosamine is conjugated to, or a conjugate of the invention is co-administered with, a topoisomerase 1 inhibitor to treat cancer. In one embodiment, the cancer is metastatic carcinoma of the ovary, colon, or rectum, or small cell lung cancer.

Topoisomerase 2 inhibitors useful in the practice of the present invention include but are not limited to etoposide, VP-16 (Vepesid), teniposide, VM-26 (Vumon), and etoposide phosphate (Etopophos). In accordance with the methods of the present invention, glucose or 2-DG or a derivative thereof such as glucosamine is conjugated to, or a conjugate of the invention is co-administered with, a topoisomerase 2 inhibitor to treat cancer. In one embodiment, the cancer is refractory testicular tumors, refractory acute lymphoblastic leukemia (ALL), or small cell lung cancer.

Tyrosine kinase inhibitors useful in the practice of the present invention include but are not limited to imatinib (Gleevec). In accordance with the methods of the present invention, glucose or 2-DG or a derivative thereof such as glucosamine is conjugated to, or a conjugate of the invention is co-administered with, a tyrosine kinase inhibitor to treat cancer. In one embodiment, the cancer is CML or metastatic or unresectable malignant gastrointestinal stromal tumors.

Thus, the present invention provides methods of treating cancer in which 2-DG or a derivative thereof is conjugated to an anti-neoplastic agent and the conjugate or a pharmaceutically acceptable salt thereof and one or more additional anti-cancer agents are administered to a patient. Specific embodiments of such other anti-cancer agents suitable for use in forming a conjugate of the invention or for co-administration with a conjugate of the invention include without limitation 5-methyl-6-[[(3,4,5-trimethoxyphenyl) amino]-methyl]-2,4-quinazolinediamine or a pharmaceutically acceptable salt thereof, (8S,10S)-10-(3-amino-2,3,6-trideoxy-.alpha.-L-lyxo-hexopyranosyl)oxy]-8-glycoloyl-7, 8,9,10-tetrahydro-6,8,11-trihydroxy-1-methoxy-5,12-naphthacenedione or a pharmaceutically acceptable salt thereof; 5-fluoro-2,4(1H,3H)-pyrimidinedione or a pharmaceutically acceptable salt thereof; 2-amino-1,7-dihydro-6H-purine-6-thione or a pharmaceutically acceptable salt thereof; 22-oxo-vincaleukoblastine or a pharmaceutically acceptable salt thereof; 2-bis[(2-chloroethyl)amino]tetrahydro-2H-1,3,2-oxazaphosphorine, 2-oxide, or a pharmaceutically acceptable salt thereof; N-[4-[[(2,4-diamino-6-pteridinyl)methyl]-methylamino]benzoyl]-L-glutamic acid, or a pharmaceutically acceptable salt thereof; or cis-diamminedichloroplatinum (II).

4. Site of Attachment Considerations

Some structures are preferred for the conjugates used in the present methods. For example, the 2 position of D-glucose, 2-deoxyglucose, and 2-glucosamine is a preferred site of attachment for the linker in the conjugates of the invention. Other sites of attachment are not preferred. For example, the hydroxy group at the 6 position of D-glucose, deoxyglucose, and glucosamine is phosphorylated upon entry into a cell, and the presence of the phosphate group inhibits diffusion of the resulting compound from the cell. With conjugates carrying an anti-neoplastic agent at this position, phosphorylation cannot occur. Accordingly, conjugates of 2-deoxyglucose are preferred wherein the anti-neoplastic agent is attached at a position other than the 6-position. In one embodiment, the anti-neoplastic agent is attached at the 2-position. Alternative conjugates can be prepared wherein the anti-neoplastic agent is attached to the 3-position or 4-position, although such conjugates may not be rapidly phosphorylated, if at all. A conjugate that can be rapidly phosphorylated after incorporation in the cells, with the consequence that the conjugate remains in the cell, is a preferred conjugate of the invention. Accumulation of the conjugate in the cells provides greater certainty that the cell will be killed by the conjugate.

Accordingly, in one group of preferred embodiments, the glucose-anti-neoplastic agent conjugate has the formula:

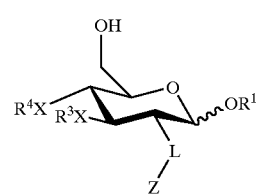

Ia wherein L is a bond or linking group; Z is an anti-neoplastic agent; each X is independently selected from the group consisting of O and NH; $R^1$, $R^3$ and $R^4$ are each members independently selected from the group consisting of H, ($C_1$–$C_{12}$)alkyl, ($C_1$–$C_{12}$)acyl and a solubility or partitioning effector component. In a preferred embodiment, L is not linked to the deoxyglucose moiety by an ester bond, as such bonds are rapidly cleaved by esterases in vivo. The solubility or partitioning effector component can be essentially any component that increases the solubility of the resultant conjugate in aqueous solution, relative to the conjugate having a hydrogen atom at the same position. Suitable solubility or partitioning effector components include oligoethylene glycol, oligopropylene glycol, polyhydroxylated carbon chains (typically one to thirty carbons in length) and the like.

In one group of most preferred embodiments, the glucose-anti-neoplastic agent conjugate has the formula Ia in which each X is O, and $R^1$, $R^3$ and $R^4$ are each H. In another group of most preferred embodiments, the glucose-anti-neoplastic agent conjugate has the formula Ia in which each X is O, and two of $R^1$, $R^3$ and $R^4$ are H, with the remaining member of $R^1$, $R^3$ and $R^4$ being a solubility or partitioning effector component.

Still further preferred are those glucose-anti-neoplastic agent conjugates having the formula:

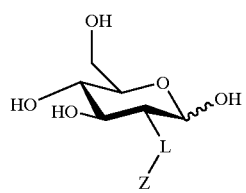

Ib wherein L is a linking group; and Z is an anti-neoplastic agent. Particularly preferred are those conjugates of anti-neoplastic agents that have been approved for the treatment of certain cancers including lung cancer, ovarian cancer, prostate cancer and colon cancer. Accordingly, preferred conjugates for use in treating lung cancer are those conjugates of formula Ib in which Z is selected from cyclophosphamide, doxorubicin, vincristine, etoposide and cisplatin. Preferred conjugates for use in treating ovarian cancer include those conjugates of formula Ib in which Z is selected from cisplatin, carboplatin, cyclophosphamide, ifosfamide, melphalan, chlorambucil and thiotepa. Preferred conjugates for use in treating prostate cancer include those conjugates of formula Ib in which Z is selected from estramustine, estramustine phosphate, prednimustine, cisplatin, 5-fluorouracil, melphalan and hydroxyurea. A preferred conjugate for use in treating colon cancer is a conjugate of formula Ib in which Z is 5-fluorouracil.

In still other particularly preferred embodiments, the glucose-anti-neoplastic agent conjugates are those conjugates having an appended chelating group, preferably further comprising a metal atom such as iron, gadolinium, yttrium or indium. A variety of suitable chelating agents are known to those of skill in the art and are described in, for example, Yu et al., U.S. Pat. No. 6,004,529 and Cutler et al., 2000, Cancer Biother. Radiopharm. 15(6): 531–45. More preferably, the chelate is DOTA and the metal atom is selected from $^{90}$yttrium, $^{111}$indium, $^{56}$iron, and $^{157}$gadolinium.

In still other particularly preferred embodiments, the anti-neoplastic agent is a linear or branched alkyl, alkenyl, or alkyl, or an aliphatic or aromatic cyclic group or heterocycle of 6 to 24 atoms, preferably 6 to 12 atoms, substituted with a radionuclide selected from the group consisting of $^{18}$F, $^{125}$I, $^{131}$I, $^{186}$Re, and $^{188}$Re. In a preferred embodiment of this aspect of the invention, the deoxyglucose derivative is D-glucosamine, the anti-neoplastic agent is an aromatic group substituted with a radionuclide, and the linker is an amide linker.

In a related aspect of the invention, labeled 2-deoxyglucose compounds can be used directly for cancer therapy, wherein the label is a β-emitting carbon such as $^{11}$carbon or $^{14}$carbon. Accordingly, the invention further provides a method for treating cancer in a subject in need thereof, by administering to the subject an effective amount of a β-emitting carbon-labeled 2-deoxyglucose.

Formulation and Packaging of Conjugate

The present invention provides a pharmaceutically acceptable formulation of conjugate useful in the methods of the present invention. In one embodiment, the formulation is crystalline in nature, and the conjugate is packaged in a sachet that is decanted into a potable liquid for oral administration to the patient. In this embodiment, the liquid can be a syrup or, more conveniently, a commonly consumed liquid, such as water, fruit juice, or cola. In some embodiments, the liquid will be glucose-free. In another embodiment, the conjugate is formulated as a tablet or pill containing conjugate in an amount in the range of about 100 mg to about 10 g. In some embodiments, each tablet or pill contains about 1 g of conjugate. In other embodiments, each tablet or pill contains about 5 g of conjugate.

A decided practical advantage of the compounds of the present invention is that the compounds can be administered in any convenient manner such as by the oral, intravenous, intramuscular, topical, or subcutaneous routes.

Thus, conjugate can be orally administered, for example, with an inert diluent or with an assimilable edible carrier, or it can be enclosed in hard or soft shell gelatin capsules, or compressed into tablets, or incorporated directly with the food of the diet. For oral therapeutic administration, conjugate can be incorporated with excipients and used in the form of ingestible tablets, buccal tablets, troches, capsules, elixirs, suspensions, syrups, wafers, and the like. Such compositions and preparations contain enough of the active agent to deliver the therapeutically active doses described above.

The tablets, troches, pills, capsules, and the like may also contain the following: a binder such as gum tragacanth, acacia, corn starch, or gelatin; excipients such as dicalcium phosphate; a disintegrating agent such as corn starch, potato starch, alginic acid, and the like; a lubricant such as magnesium stearate; a sweetening agent such as saccharin; and/or a flavoring agent such as peppermint, oil of wintergreen, or cherry flavoring. When the dosage unit form is a capsule, it can contain, in addition to materials of the above types, a liquid carrier. Various other materials can be present as coatings or to otherwise modify the physical form of the dosage unit. For instance, tablets, pills, or capsules can be coated with shellac. A syrup or elixir can contain the active compound, a sweetening agent, methyl and propylparabens as preservatives, and a flavoring such as cherry or orange flavor. Of course, any material used in preparing any dosage unit form should be pharmaceutically pure and substantially non-toxic in the amounts employed. In addition, the active compound can be incorporated into sustained-release preparations and formulations. The conjugate can also be administered parenterally or intraperitoneally. A solution of the active compound as a free acid or pharmacologically acceptable salt can be prepared in water suitably mixed with a surfactant such as hydroxypropylcellulose. Dispersions can also be prepared in glycerol, liquid polyethylene glycols and mixtures thereof, and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and, in final form, must be fluid to the extent that easy syringability exists. It must be stale under the conditions of manufacture and storage and must be preserved against the contaminating action of microorganisms such as bacteria and fungi.

The pharmaceutical forms suitable for topical use include oil and water emulsions and liposomal formulations, as well as lotions, creams, and ointments commonly used for topical administration of drugs.

The carrier can be a solvent or dispersion medium containing, for example, water, ethanol, polyol, for example, glycerol, propylene glycol, and liquid polyethylene glycol, and the like, suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various anti-bacterial and anti-fungal agents, for example, parabens, chlorobutanol, phenol, sorbic acid, thimerosal, and the like. In many cases, it will be preferable to include isotonic agents, for example sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique, which yield a powder of the active ingredient plus any additional desired ingredient from previously sterile filtered solution thereof.

As used herein, a "pharmaceutically acceptable carrier" includes any and all solvents, dispersion media, coatings, antibacterial and antifungal agents, isotonic agents, absorption delaying agents, and the like. The use of such media and agents for pharmaceutical active substances is well known in the art. Except insofar as any conventional media or agent is incompatible with the active ingredient, its use in the therapeutic compositions of the invention is contemplated. Supplementary active ingredients can be incorporated into the compositions of the invention.

It is essentially advantageous to formulate parental and other compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on the patient and cancer to be treated and can vary from patient to patient and cancer to cancer, but generally, a dosage unit form contains from about 100 mg to about 5 g of conjugate. Typical unit forms can contain about 0.5 to about 1 g of conjugate.

E. Kits for Cancer Treatment

The present invention provides kits with unit doses of the conjugates of Formula I, in oral and injectable dose forms. In addition to the containers containing the unit doses (either oral or injectable), these kits can contain an informational package insert describing the use and attendant benefits of the conjugate for the treatment of cancer, in particular solid tumor cancers such as lung cancer, breast cancer, ovarian cancer, prostate cancer and colon cancer.

The following examples illustrate certain aspects of the inventions, including the synthesis of conjugates of the invention and the demonstration that certain glucose conjugates of the invention are taken up by cancer cells.

EXAMPLE 1

Synthesis of Glucosamine-Camptothecin Conjugate

This example illustrates the preparation of a camptothecin-glucosamine conjugate having an acetate ester non-releasable linkage. 10-Hydroxy-camptothecin acetate salt (5 mg) was dissolved in 0.5 mL anhydrous DMF. Sodium carbonate (7.2 mg) and diisopropyl ethyl amine (12 $\mu$L) were added, followed by t-butyl bromoacetate (6 $\mu$L). After stirring for 4 days at 37° F., the 10-position alkylated product was produced as the nearly sole product. The product was of faster mobility on thin layer chromatography (TLC silica plate with 5% $H_2O$ in acetonitrile) relative to the starting material. The reaction mixture was evaporated under vacuum, dissolved in methylene chloride and extracted with $H_2O$. The organic layer was separated, concentrated under vacuum and treated with neat trifluoroacetic acid (1 mL) for 1 hour to deprotect the t-butyl ester, leaving the free carboxylic acid. Volatile components were removed under vacuum, and the acid product was dissolved in 30% butanol/methylene chloride and extracted with aqueous 5% HCl. The aqueous layer was reextracted with a fresh portion of butanol/methylene chloride. The organic layers were combined, evaporated under vacuum, dissolved in 0.5 mL of anhydrous DMF and converted to an active ester with 1-ethyl-3-(3-dimethyl aminopropyl) carbodiimide hydrochloride (4 mg) and N-hydroxysuccinimide (2.3 mg) for 2 hours. A solution of glucosamine hydrochloride (15 mg in 0.25 mL of $H_2O$) and of triethylamine (10 $\mu$L) were added. The reaction was stirred 3 days and concentrated under vacuum. The gum was dissolved in a minimum amount of methanol and purified by silica gel preparative TLC using 10% $H_2O$/MeCN as the developing solvent. The resulting glucosamine-camptothecin conjugate was dissolved and stored in a mildly acidic 1 mM $NaH_2PO_4$ buffer. The conjugate exhibited an absorption maximum of 380 nanometers and a strong blue fluorescence useful for analytical tracking.

EXAMPLE 2

Synthesis of a DOTA-Glucosamine Conjugate

This example illustrates the synthesis of a DOTA-glucosamine conjugate. Tri-t-butyl-DOTA (4,7,10-tri-(t-butyloxycarbonylmethyl)-1,4,7,10-tetraazacyclododecan-1-yl-acetic acid, 50 mg, 87 micromoles, from Bachem) was dissolved in 300 microliters of DMSO, and 12 microliters (87 micromoles) triethylamine was added, followed by 42 mg (95 micromoles) of BOP (benzotriazol-1-yloxy)tris(dimethylamino)-phosphonium hexafluorophosphate). The reaction mixture was stirred for 1 hour at room temperature followed by the addition of a solution of glucosamine HCl (21 mg, 95 micromoles) and triethylamine (13.3 microliters, 95 micromoles) in 450 microliters of $H_2O$/DMSO (1/2 by volume).

The resulting mixture was stirred for two days at room temperature, and solvent was removed by evaporation under reduced pressure. The resulting oil was dissolved in 0.5 mL of MeOH and precipitated into 5 mL of diethyl ether. The supernatant was recovered and concentrated under reduced pressure. This material was purified on a silica gel column via elution using methylene chloride followed by increasing concentrations of MeOH. The product eluted with 20% MeOH in methylene chloride. Product fractions were detected by $H_2SO_4$ charring on TLC plates. Product fractions were concentrated and deprotected (removing t-butyl group) using 1 mL of trifluoroacetic acid for 2 hrs at room temperature followed by evaporation under reduced pressure. The product was dissolved in 1 mL of deionized $H_2O$ and extracted with methylene chloride. The aqueous layer was evaporated under reduced pressure to yield 29 mg of product.

Mass spectrometric analysis using negative ion electrospray ionization confirmed the expected molecular weight of 565 from a solution of the compound in 50 mM $NH_4OH$ ($MeOH/H_2O$) (4/1 by volume).

EXAMPLE 3

Uptake of the DOTA-Glucosamine Conjugate

This example illustrates the uptake of the DOTA-glucosamine conjugate prepared in Example 2 in Raji lymphoma cells. The cells used were Raji cells from culture in one t-75 flask. The reagents used were Phosphate Buffered Saline, DOTA-glucosamine conjugate, Indium-111 chloride salt, Indium Chloride, and Cytochalasin B (Sigma, in a stock solution of 1 mg/mL water).

Labeling DOTA-Glucose with Indium

To 60 µL DOTA-glucosamine in ammonium acetate buffer (pH 6.5) were added 2 µL of Indium-111. The resulting mixture was incubated for 1 hr at 37° C. An equimolar amount of non-radiolabeled Indium chloride was added, and the mixture was incubated for an additional 1 hr at 37° C. The resultant mixture was applied to a Chelex polyanionic ion-exchange column in deionized $H_2O$, and the flow-through was collected. The uptake reaction was carried out as follows. First, 15 mL of culture medium with Raji cells was centrifuged for 10 min. at 800×g; then, the cells were resuspended in PBS (pH 7.4) and recentrifuged for 10 min. at 800×g; then, the cells were resuspended in 1.5 mL of PBS (pH 7.4), and the resulting suspension was aliquoted into eight reaction tubes at 200 uL per tube.

About 380,000 CPM of the DOTA-Glucosamine conjugate were added to each tube, and at 0, 30, 60, and 120 min. time points, two tubes, one to which a final concentration of 50 µM cytochalasin B had been added and one to which cytochalasin B had not been added, were removed from incubation at 37° C. and immediately put on ice. The cells from each tube were washed twice with PBS and resuspended in 100 µL PBS; then, the radioactivity was counted using a Wallac gamma counter. The results are provided as a histogram in FIG. 1.

EXAMPLE 4

Synthesis of a Carboplatinum-Glucosamine Conjugate

This example describes the synthesis of a carboplatinum-glucosamine conjugate of the invention by the synthetic scheme illustrated below.

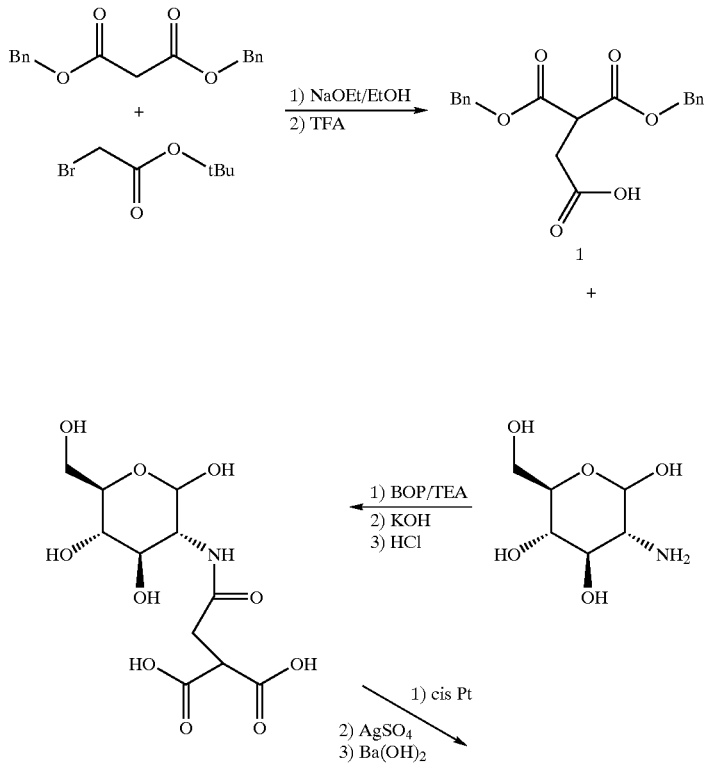

-continued

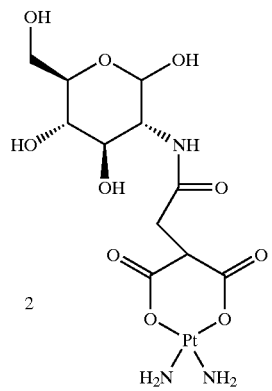

2

To prepare the conjugate, 175 microliters (0.704 millimoles) of dibenzylmalonate and 91 microliters (0.704 millimoles) of bromo tertiary-butyl acetate were dissolved in 2 ml of absolute ethanol. Then, 0.704 millimoles of sodium ethoxide in a minimum of ethanol was added and the solution was stirred at 80° C. for 1 hour, cooled to 20° C., and extracted with ethyl acetate and water buffered with potassium dihydrogen phosphate. The organic phase was evaporated under centrifugation and then treated with 1 ml of trifluoroacetic acid at 20° C. for 1 hour, evaporated under centrifugation, and extracted with 1 molar HCl and methylene chloride containing 10% BuOH. The organic layer was evaporated under centrifugation, acetonitrile was added, and the solution was evaporated under centrifugation. These steps yielded 150 mg of the acid compound labeled as (1) in the synthetic scheme shown above.

The acid compound (compound (1) in the synthetic scheme above, 150 mg, 0.34 millimoles) was treated with 149 mg (0.34 millimoles) of benzotriasol-1-yloxy-tris(dimethylamino)-phosphonium hexafluorophosphate (BOP) and 47 microliters (0.34 millimoles) of triethyl amime in 1 ml of dry DMF for 15 minutes followed by the addition of 73 mg (0.35 millimoles) of glucosamine HCl and 47 microliters (0.34 millimoles) of triethyl amine. This solution was stirred at 20° C. for 24 hrs. The reaction mixture was precipitated into 20 ml of methylene chloride, and the supernatant was recovered and evaporated. Residue was dissolved in a minimum volume of ethanol, diluted with ethyl acetate and loaded on a silica gel column and eluted with 30% ethanol in ethyl acetate. Early fractions yielded 44 mg of the product upon evaporation. The benzyl groups were removed by treatment with 1 ml of 0.5 molar potassium hydroxide for 2 hours at 20° C. The solution was converted into the free acids by passage through a sulfonic acid Dowex column, and evaporated and dissolved into 2 ml of water, making a 50 millimolar stock solution of the glucosamine malonic acid conjugate.

The carboplatinum conjugate compound, compound (2) in the synthetic scheme above, was prepared as follows. About 10 mg of cis diamino dichloro platinum (cisplatinum) were dissolved in 10 ml of distilled water, and 10.4 mg of silver sulfate in 2 ml of water were added with stirring; after 30 minutes, a precipitate had formed, and the suspension was centrifuged. About 9.6 ml of the supernatant was decanted, and 0.66 ml of 50 millimolar of the glucosamine malonic acid conjugate from above was added, and the resulting mixture was stirred for 30 minutes. Then, 8.3 mg of barium hydroxide-8H$_2$O in 1 ml of water were added to the solution. After 30 minutes of stirring, the suspension was centrifuged to precipitate the barium sulfate. The supernatant was evaporated under centrifugation, and the precipitate was redissolved in water to produce a 10 millimolar stock solution of the desired conjugate compound (2) shown in the synthetic scheme above.

EXAMPLE 5

Synthesis of a Mitomycin C-Glucosamine Conjugate

This example describes the synthesis of a Mitomycin C-glucosamine conjugate of the invention by the synthetic scheme shown below.

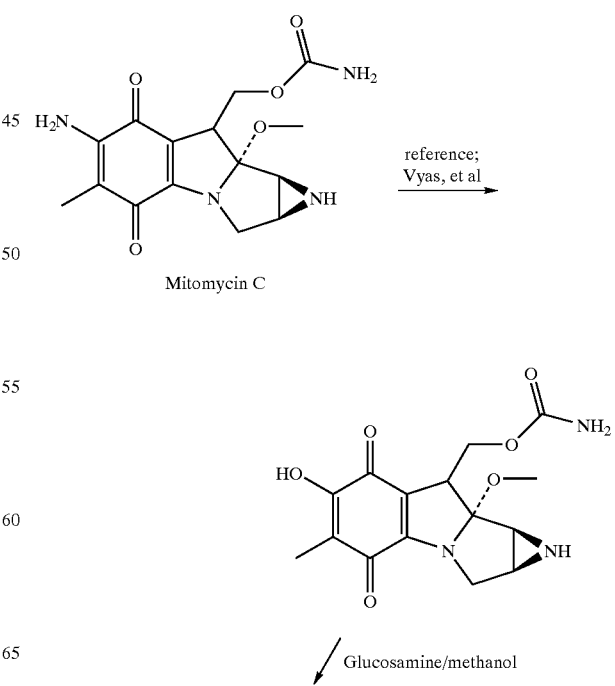

-continued

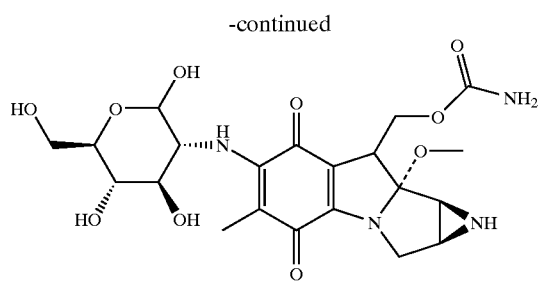

Mitomycin C, a commercially available reagent, is first subjected to hydrolysis of the amino quinine moiety as described in the reference "The Practical Synthesis of Mitomycin A", Vyas et al., 1986, *J. Org. Chem.* 51: 4307–4309, incorporated herein by reference. The formation of the glucosamine conjugate is accomplished by an exchange reaction that has been done using many other amines, as described in the reference "Development of New Mitomycin C and Porfiromycin Analogues", Iyengar et al., 1981, *J. Med. Chem.* 24: 975–981, incorporated herein by reference.

EXAMPLE 6

Synthesis of a Methotrexate-Glucosamine Conjugate

This example describes the synthesis of a methotrexate-glucosamine conjugate of the invention by the synthetic scheme shown below.

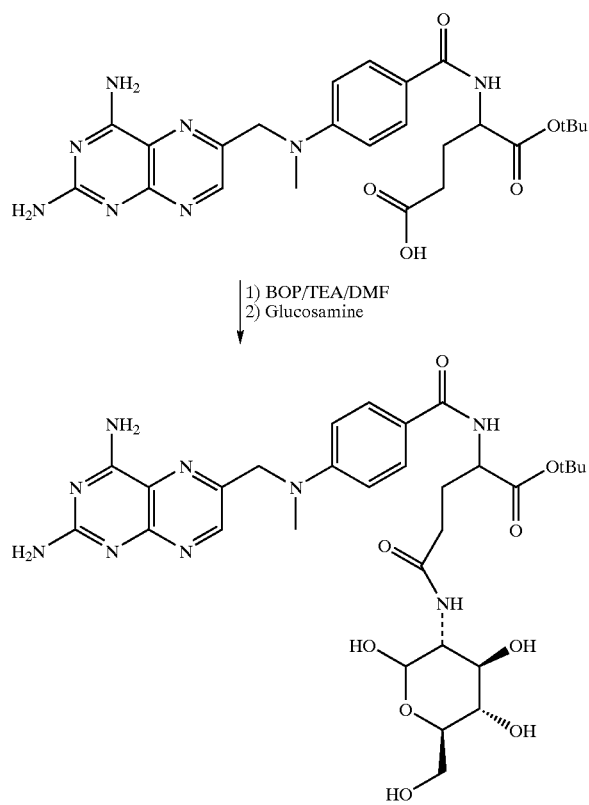

The starting methotrexate alpha t-butyl ester is obtained from commercially available starting materials, and the conjugate synthesized by a procedure substantially similar to the procedure described in the reference "Selective Coupling of Methotrexate to Peptide Hormone Carriers", Nagy et al., 1993, *Proc. Natl. Acad. Sci.* 90: 6373–6376, incorporated herein by reference, for coupling methotrexate to amino groups of peptides.

EXAMPLE 7

Synthesis of an Anthramycin (pyrrolo[1,4]benzodiazepine)-Glucosamine Conjugate

This example describes the synthesis of an anthramycin (pyrrolo[1,4]benzodiazepine)-glucosamine conjugate of the invention by the synthetic scheme shown below.

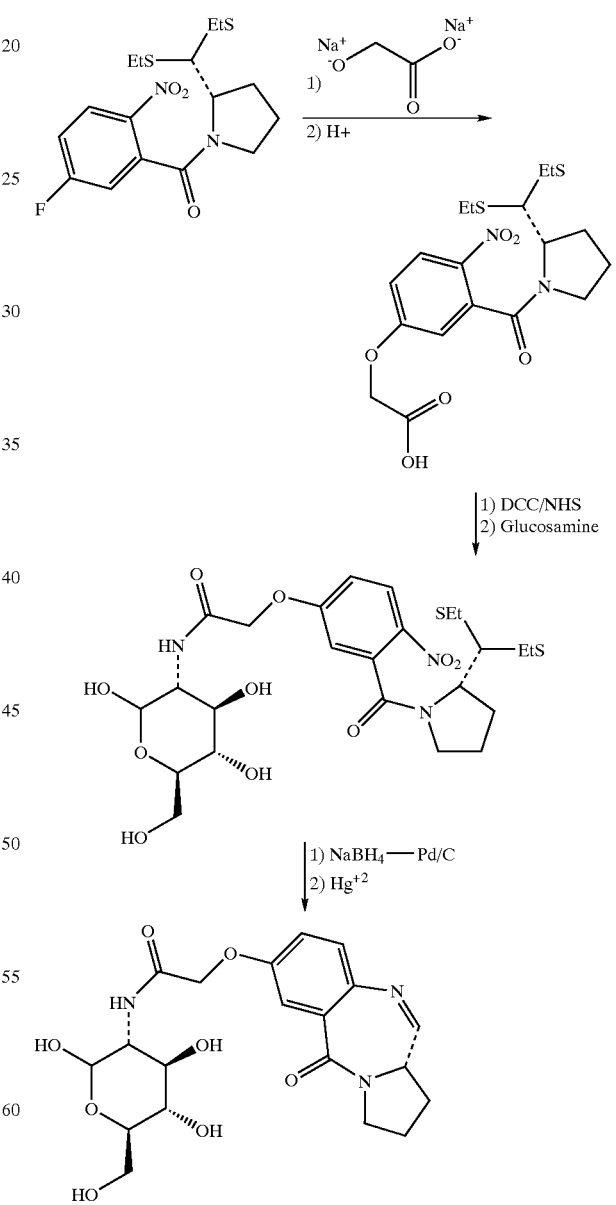

The starting material shown in the synthetic scheme above is prepared in accordance with the procedure described in the reference "Synthesis and DNA Crosslinking Ability of a Dimeric Anthramycin Analog", Farmer et al., 1988, *Tetrahedron Letters* 29, 5105–5108, incorporated herein by reference. The displacement of fluorine with the sodium salt of hydroxyacetic acid is performed in a manner analogous to the sodium alkoxide displacements described in the Farmer et al. reference. The coupling of the free acid to glucosamine using dicyclohexylcarbodiimide (DCC) and-N hydroxysuccinimide (NHS) is accomplished by any standard amide bond formation procedure. Suitable deprotection conditions for the completion of the anthramycin moiety are described in the Farmer et al. reference.

EXAMPLE 8

Synthesis of Iodo-Containing Conjugates

This example describes the synthesis of a number of iodo-containing conjugates compounds of the invention. As described below, these compounds can be readily modified to include a radioactive iodo moiety, such as $I^{125}$ or $I^{131}$, that acts as the cytotoxic moiety in the conjugate. In the reactions described below, tertiary amines such as $NEt_3$ or DIEA can be used interchangeably, although the latter may be preferred if where $NEt_3$ is considered reactive enough to attack the electrophile. In addition, while, in most instances, the free base glucosamine was generated in situ by addition of tertiary amines or aqueous bicarbonate, in some instances it is possible to form the free amine (in water or DMF/water), remove the volatiles, and extract it into the reaction with DMF or a suitable solvent.

A. Synthesis of 4-iodo-N-benzoyl-glucosamine (Compound TP010)

To a solution of 4-iodobenzoic acid (1 mmol) in DMF (2 mL) was added pentafluorophenol (2 mmol) and diisopropylcarbodiimide (1.2 mmol). The solution was stirred at room temperature for 6 hours and then added to a solution of glucosamine hydrochloride (1 mmol) and $NEt_3$ (2 mmol) in DMF/$H_2O$ (1 mL, 1:10 v/v). The reaction was stirred for 16 hours and then crystallized from hot water to yield 4-iodobenzoyl glucosamine, compound TP010. The structure of TP010 is shown below (R is I).

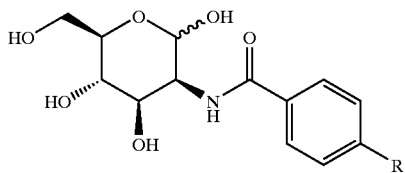

As described in part K of this Example, a conjugate of the invention ($^{131}$I-TP010) can be formed from TP010 by converting the iodine in TP010 to the radioactive $^{131}$I isotope. The structure of the resulting compound is the same as TP010, except that R is $^{131}$I. The conjugate $^{131}$I-TP010 can be formed not only from TP010, via a trimethyl (or other lower alkyl) tin, derivative but from a number of other intermediate compounds of the invention as well. Such intermediate compounds of the invention thus include but are not limited to compounds in which R in the structure above is selected from the group consisting of $SnMe_3$, $SnX_3$, where X is a linear or branched $C_1$–$C_6$ alkyl, Br, triflate ($OSO_2CF_3$), amino, or protected amino group (suitable protecting groups include t-BOC, f-MOC, and other protecting groups used in peptide synthesis).

$^{131}$I-containing conjugates of the invention can be administered in accordance with the methods of the invention by intravenous injection (see part L of this Example). Thus, the present invention provides pharmaceutical formulations of such compounds suitable for injection. Such formulations can include, for example, sterile saline, a preservative, and a buffer. In addition, such formulations will typically comprise a mixture of the pharmaceutically active conjugate of the invention as well as its non-radioactive counterpart. Thus, one illustrative pharmaceutical formulation of the invention comprises both TP010 and $^{131}$I-TP010.

Different substituted iodobenzoyl glucosamine (as well as galactosamine and mannosamine) derivatives were (or can be) synthesized following the general procedure described below. Also, aromatic, iodine bearing heterocyclic carboxylic acids can be converted to the respective 2-glucosamine, 2-galactosamine or 2-mannosamine derivatives in the manner described.

Furthermore, a variety of substituents other than the iodobenzyl substituent shown above can be used in the conjugates of the invention. Thus, while the iodo moiety is in the para position in TP010, it can also be located in an ortho or meta position, although the para position is preferred. In addition, the iodobenzyl group can have one or more fluorine moieties attached to the benzyl ring, at any position. The iodobenzyl group can be replaced with an iodoheteroaryl group, in which the heteroaryl moiety may be a 5 or 6-membered ring and in which the heteroatom or atoms are O, S, and N, and in which one or more hydrogens attached to the ring are replaced with one or more fluorine atoms. Thus, the heteroaryl group can be a thiophene, furan, pyrrole, pyridine, or pyrimidine. In addition, in any of the foregoing compounds, the NHCO linker can be replaced with an NHCHR linker or an NHCHRCO linker, in which R is H, methyl, or mono-, di-, or tri-fluoromethyl. The synthesis schemes for a variety of such compounds are illustrated below and in the remainder of this Example.

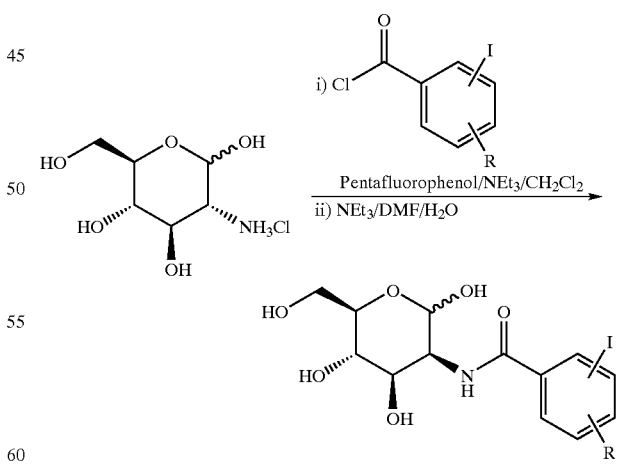

TP026: I = 2-iodo, R = H
TP027: I = 3-iodo, R = H
TP030: I = 5-iodo, R = 2-fluoro
TP031: I = 3-iodo, R = 4-methyl
TP032: I = 5-iodo, R = 3-bromo
TP035: I = 5-iodo, R = 2-fluoro

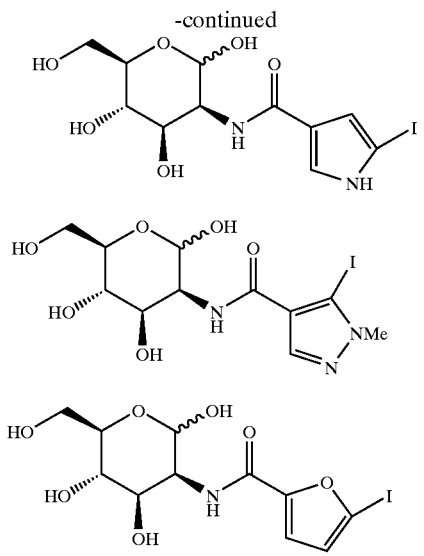

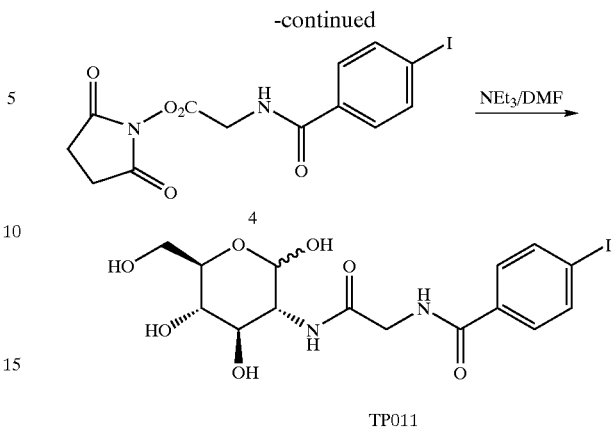

The substituted iodobenzoic acids (1 mmol) were reacted with oxalyl chloride (1 mL) and DMF (1 drop) for 10–30 min. Volatiles were removed in vacuo to yield the acid chloride, to which was added a solution of pentafluorophenol (1.2–2 mmol) and NEt$_3$ (3 mmol, an excess doesn't affect the outcome of the reaction) in dichloromethane (2 mL). The mixture was stirred for ca 30 min and the volatiles removed in vacuo. To this residue was added a solution of the amino-sugar hydrochloride (1–2 mmol), NEt$_3$ (3 mmol) in DMF/water (1 mL, 0.2 mL respectively) and stirred for 18 h. Volatiles were removed in vacuo. The residue was extracted with ether (2×15 mL) and the remaining solid crystallized from hot water.

B. Synthesis of 4-iodohippuroyl glucosamine (Compound TP011)

The compound 4-iodohippuroyl glucosamine was made in accordance with the synthetic scheme below.

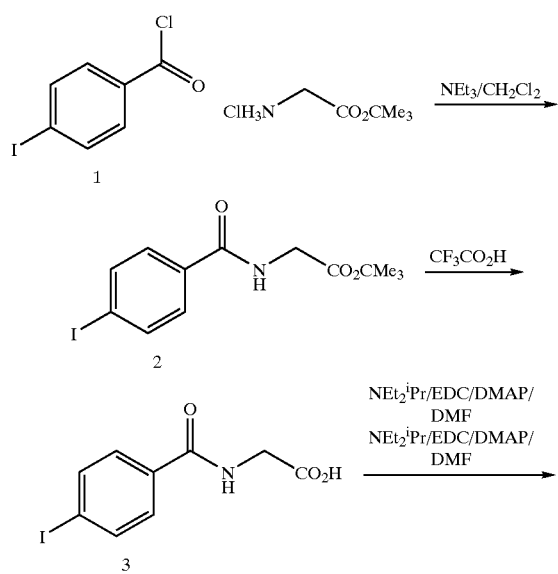

To a solution of tertiarybutylglycine hydrochloride (12 mmol) and NEt$_3$ (28 mmol) in CH$_2$Cl$_2$ (15 mL) was added dropwise a solution of 4-iodobenzoyl chloride (11 mmol) in CH$_2$Cl$_2$ (5 mL) and the reaction mixture stirred for 2 hours. Then, the reaction mixture was diluted with CH$_2$Cl$_2$ (30 mL), washed with water (2×10 mL), then with saturated aqueous KHSO$_4$ (2×10 mL), then with saturated aqueous NaHCO$_3$ (10 mL), and then with brine (20 mL), and then, the reaction mixture was dried over anhydrous Na$_2$SO$_4$. Volatiles were removed in vacuo to yield 3.7 g of compound 2 in the scheme above as a white solid, which was used for the next reaction.

A mixture of TFA and CH$_2$Cl$_2$ (4:1, 5 mL) was added to the t Butyl ester (compound 2 in the scheme above, 10 mmol), and the reaction mixture was stirred for 3 hours. Volatiles were removed in a rotavap (centrifugation under vacuum) after adding toluene (5 mL). The remaining white solid (compound 3 in the scheme above, 3.1 g) was used directly for the following reaction.

To a solution of the acid (compound 3 in the scheme above, 1.7 mmol) in DMF (2 mL) was added EDC (2.6 mmol) and N-Hydroxysuccinimide (4.3 mmol), and the reaction was stirred overnight. Volatiles were removed in a rotavap, and the residue was dissolved in EtOAc (50 mL) and washed with saturated aqueous NaHCO$_3$ (5×15 mL), water, and brine (20 mL). After the resulting mixture was dryied over anhydrous Na$_2$SO$_4$, the volatiles were removed in a rotavap, and the crude mixture was separated on a Si-gel column using EtOAc as the solvent to isolate 0.1 g (26%) of compound 4 in the scheme above as a white solid.

To a slurry of Glucosamine hydrochloride (0.08 g, 0.37 mmol) and NEt$_3$ (1.0 mL, 7 mmol) in DMF (1 mL) was added the succinimidite ester (compound 4 in the scheme above, 0.15 mmol), and the reaction mixture was stirred at 80° C. for 1 hour and then at room temperature for 11 hours. The reaction mixture was adsorbed on Si-gel and then separated on a Si-gel column using MeCN-10% aqueous MeCN as eluent to yield 4-iodohippuroyl glucosamine, compound TP011 in the scheme above, as a white solid.

C. Synthesis of 4-iodobenzyl glucosamine (Compound TP012) and 4-iodobenzyl galactosamine The compound 4-iodobenzyl glucosamine can be made in accordance with the synthetic scheme below.

An alternate route to 4-iodobenzyl glucosamine is shown in the scheme below.

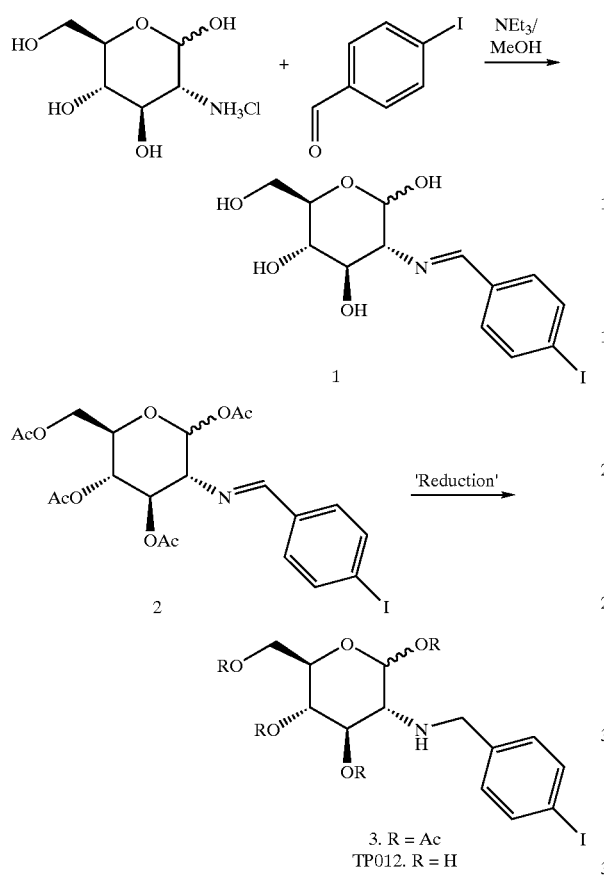

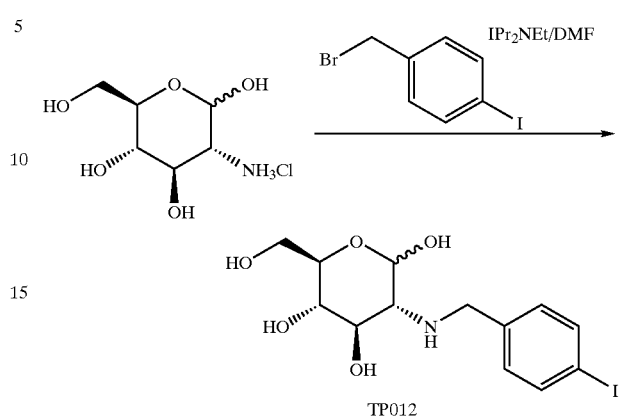

To a solution of glucosamine hydrochloride (1.2 mmol) in MeOH (4 mL) and water (0.5 mL) was added NEt₃ (1 mL) and a solution of 4-Iodobenzaldehyde (1.1 mmol), and the resulting mixture was left standing at room temperature for 24 hours. The precipitated white spangles were collected by filtration, washed with Et₂O and used for further reactions. The yield of product (compound 1 in the scheme above) was 94%.

To a slurry of 4-iodobenzylidene glucosamine (compound 1 in the scheme above) in Ac₂O and pyridine was added DMAP, and the reaction was stirred for 18 hours. Volatiles were removed in vacuo to yield the tetraacetyl derivative (compound 2 in the scheme above) in quantitative yield.

A solution of the tetraacetyl derivative (compound 2 in the scheme above) in THF is reacted with resin bound triacetoxyborohydride for 18 hours. The solution is filtered off and the resin washed with THF. Volatiles are removed in vacuo to yield the tetraaacetyl amine (compound 3 in the scheme above).

A solution of the amine (compound 3 in the scheme above) in NH₃/MeOH is stirred for 30 minutes, and the volatiles are then removed in vacuo. The residue is crystallized from MeOH-MeCN to yield 4-iodobenzyl glucosamine (compound TP012 in the scheme above).

4-Iodobenzyl galactosamine can be prepared following the route described above using galactosamine in place of glucosamine in the synthesis.

Thus, a slurry of glucosamine hydrochloride (0.7 g) and diisopropylethylamine (0.6 mL) in DMF (2.0 mL) was stirred at 80° C. for 30 minutes. A solution of 4-iodobenzylbromide (0.4 g) in DMF (2 mL) was added to the reaction mixture, and the resulting mixture stirred for 18 hours. After the reaction mixture was cooled to room temperature, the precipitated solid was removed from the supernatant by decanting. Volatiles were removed from the supernatant, and the resulting residue was separated on a si-gel column using 10% aqueous MeCN as the eluent to yield 50 mg of pure 4-iodobenzyl glucosamine (compound TP012 in the scheme above). The purity of 4-iodobenzyl bromide, which can vary greatly from batch to batch if obtained from commercial suppliers, will affect the yields of this reaction accordingly. The compound 4-Iodobenzyl galactosamine can be prepared using a similar reaction scheme, starting from galactosamine hydrochloride and iodobenzyl bromide.

Glucosamine hydrochloride, galactosamine hydrochloride and mannosamine hydrochloride was similarly converted to the 1-(4-iodophenylethyl) amine by a reaction with 1-(4-iodophenylethyl)bromide, as shown below.

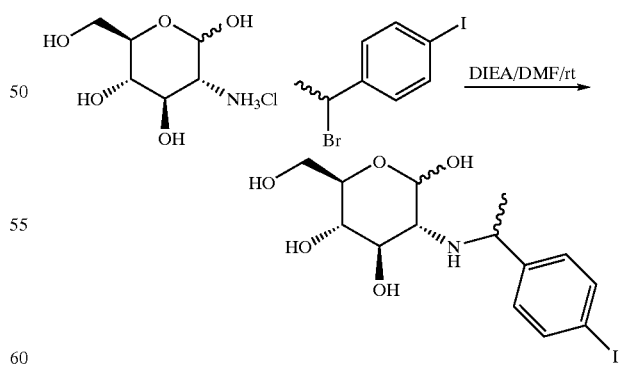

Glucosamine hydrochloride, galactosamine hydrochloride and mannosamine hydrochloride are similarly converted to the 1-(4-iodophenyl-2,2,2-trifluoroethyl) amine by a reaction with 1-(4-iodophenyl-2,2,2-trifluoroethyl)bromide, as shown below.

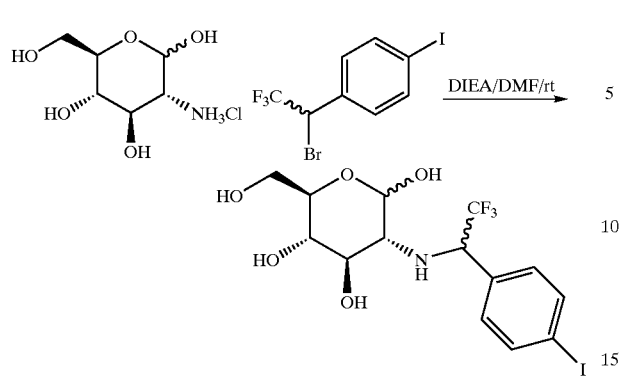

Glucosamine hydrochloride was similarly converted to 4-iodophenacyl glucosamine following the alkylation protocol described above. Galactosamine hydrochloride and mannosamine hydrochloride can be similarly converted to the respective 4-iodophenacyl derivatives using substantially similar methodology.

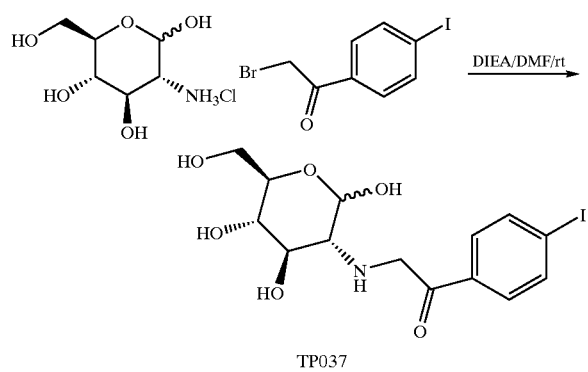

TP037

D. Synthesis of bis-Z-3-iodopropen-2-yl glucosamine (Compound TP018) and bis-E-3-iodopropen-2-yl glucosamine (Compound TP019)

The compounds bis-Z-3-iodopropen-2-yl glucosamine (Compound TP018) and bis-E-3-iodopropen-2-yl glucosamine (Compound TP019) can be made in accordance with the synthetic scheme below.

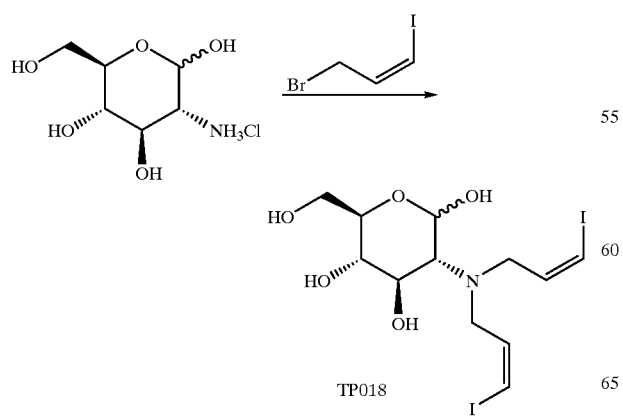

TP018

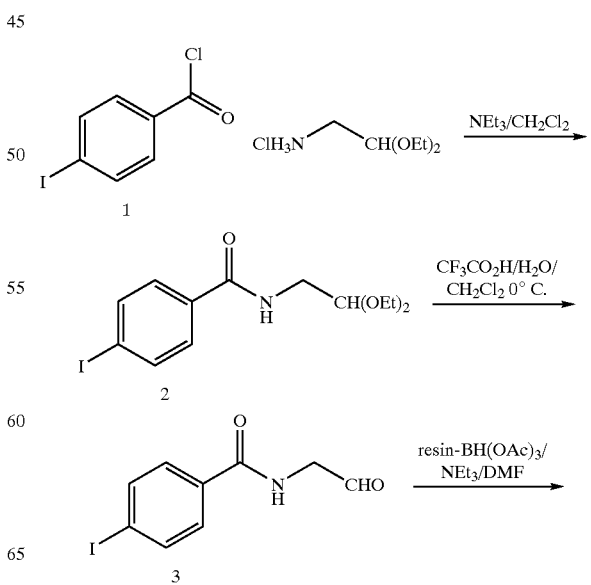

TP019

To a solution of glucosamine hydrochloride (2 mmol) and Diisopropylethyl amine (4 mmol) in DMF (2 mL) was added the allyl bromides (1 mmol) and stirred at room temperature for 18 hours. Volatiles were removed in a rotavap and the residue separated on a Si-gel column using MeCN-10% $H_2O$/MeCN to yield the compound as a solid.

Compounds TP018 and TP019 are illustrative of a variety of compounds of the invention in which an iodovinyl moiety is attached to the 2 position of glucose or a glucose analog, such as 2-deoxyglucosamine (where the linker is attached to the amine at the 2 position), via an alkyl $(CH_2)_n$, polyunsaturated alkenyl $(CH=CH)_n$, oligoglycol $(OCH_2CH_2)_n$, or oligopeptide linker, where n is 1 to 6 or more. Other points of attachment of such linkers include the 3 and 4 positions. The iodo group is attached to the linker in a manner that renders it relatively unsusceptible to deiodonation, i.e., via a —CH=I linkage.

E. Synthesis of an Aminoethyl Linked 4-iodobenzoyl glucosamine (Compound TP014)

An aminoethyl linked 4-iodobenzoyl glucosamine (Compound TP014) can be made in accordance with the synthetic scheme below.

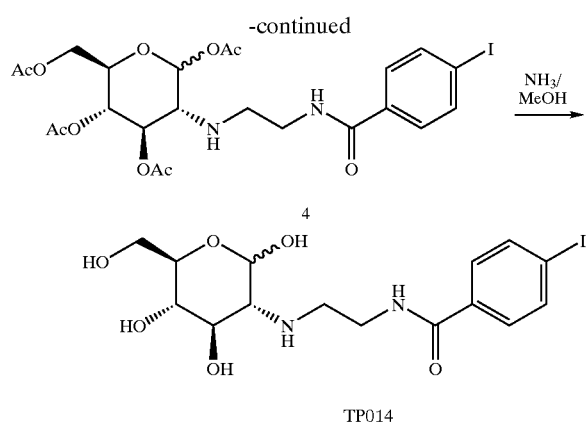

Thus, to a solution of the aminoacetal (10 mmol) and NEt₃ (14 mmol) in CH₂Cl₂ (5 mL), which had been cooled in an ice-bath, was added dropwise a solution of 4-iodobenzoyl chloride (2.0 g, 7.5 mmol) in CH₂Cl₂ (3 mL), and the reaction mixture was stirred for 2 hours. Then, the reaction mixture was diluted with CH₂Cl₂ (30 mL), washed with water (2×10 mL), then with saturated aqueous NaHCO3 (10 mL), then with brine (20 mL), and then the reaction mixture was dried over anhydrous Na₂SO₄. Volatiles were removed in vacuo to yield 2.5 g (92%) of compound 2 in the scheme above as a white solid, which was used for the next reaction.

The acetal (compound 2 in the scheme above, 0.91 mmol) was stirred in a solution of TFA (4.0 mL), water (1.0 mL) and CH₂Cl₂ (1.0 mL) for 3 hours. Volatiles were removed in a rotavap to yield (96%) compound 3 in the scheme above as a white solid.

To a slurry of tetraacetylglucosamine hydrochloride (compound 3 in the scheme above, 0.87 mmol) in DMF (2 mL) was added resin bound triacetoxyborohydride (2 mmol/g, 1.7 mmol), and the reaction mixture was stirred for 2 days. Volatiles were removed in vacuo, and the crude product, compound 4 in the scheme above, reacted with NH3/MeOH (%, mL) for 30 minutes. Volatiles were removed, and the desired compound, compound TP014 in the scheme above, was isolated upon crystallization from MeOH/MeCN.

F. Synthesis of Amide Linked glucosamine 4-iodobenzyl oligoethyleneglycol Conjugates (Including Compound TP017)

Amide linked glucosamine 4-iodobenzyl oligoethyleneglycol conjugates (such as Compound TP017) can be made in accordance with the synthetic scheme below.

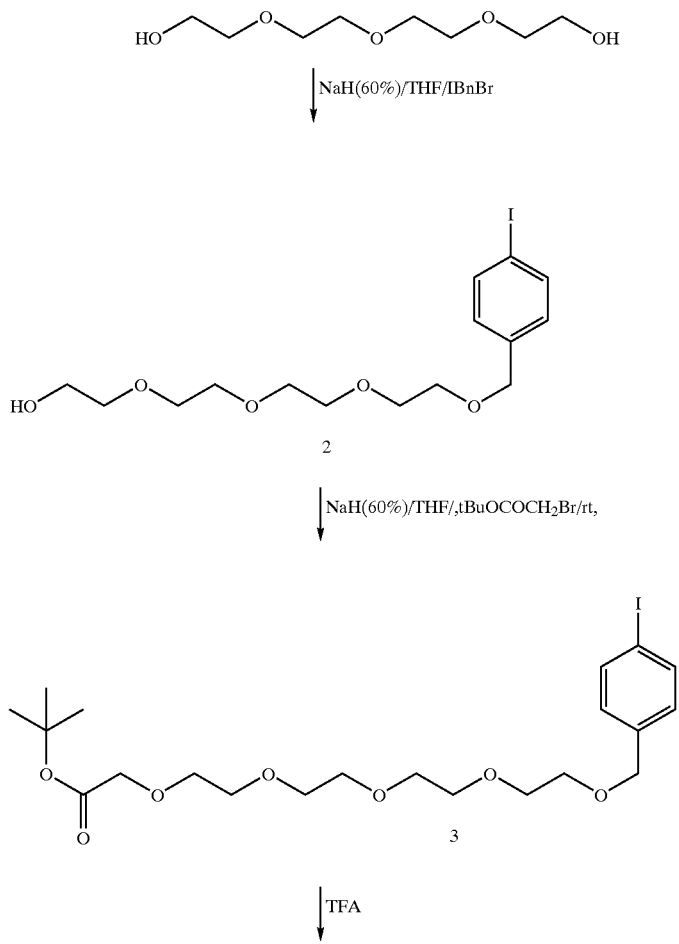

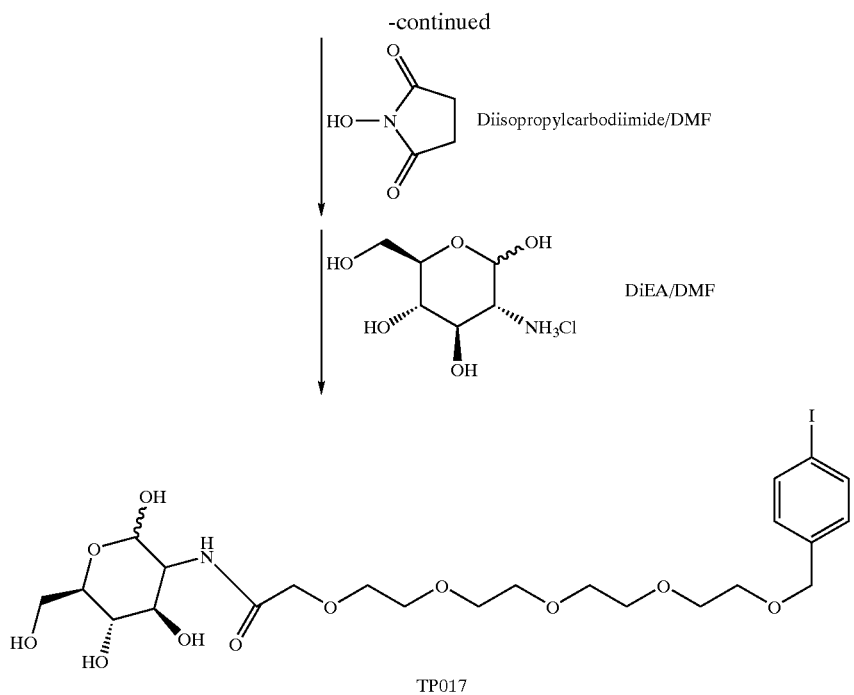

TP017

In this synthesis scheme, oligoethyleneglycol mono-4-iodobenzyl ethers are first prepared. Thus, to a solution of tetraethyleneglycol (10 mmol) in THF (15 mL) was added NaH (60% dispersion in oil, 10 mmol), and the reaction was stirred vigorously at room temperature. After 30 minutes, a solution of 4-iodobenzylbromide (10 mmol) in THF (10 mL) was added to this slurry, and stirring was continued for 3 hours at room temperature. The solid precipitate was filtered off, and the volatiles were removed in vacuo to yield a residue that was separated by Si-gel column chromatography using 80% ether/dichloromethane to 10% EtOH in ether as eluent to yield 0.8 g of the desired product (compound 2 in the scheme above) as viscous oil.

Triethyleneglycol and diethyleneglycol were similarly converted to the corresponding mono-4-iodobenzyl ethers.

Next, the oligoethyleneglycol mono-4-iodobenzyl carboxylic acid esters are prepared. Thus, to a solution of tetraethyleneglycol mono-4-iodobenzylether (1 mmol) in THF (2.0 mL) was added NaH (60% dispersion in oil, 2 mmol), and the reaction was stirred vigorously at room temperature. After 30 minutes, tertiarybutyl bromoacetate (1 mmol) was added, and stirring was continued at room temperature for 1 hour. Ether (2 mL) was added to the reaction mixture, and the reaction mixture was then filtered. The filtrate was concentrated in vacuo and separated by Si-gel column chromatography using 80% ether/dichloromethane as eluent to yield 0.4 g of the desired carboxylic acid ester product (compound 3 in the scheme above) as a viscous oil.

A solution of the carboxylic acid ester (compound 3 in the scheme above) in dichloromethane (0.5 mL) was treated with TFA (1 mL) at room temperature for 1 hour. Volatiles were removed in vacuo, and the residue was separated by Si-gel column chromatography using 20% EtOH in ether as eluent to yield 0.24 g of the free carboxylic acid as a viscous oil.

The carboxylic acids were synthesized from triethyleneglycolmonobenzyl ether and diethyleneglycolmonobenzyl ethers using similar methodology.

Next, the amide linked glucosamine 4-iodobenzyl oligoethyleneglycol conjugates were prepared. Thus, a solution of the acid (0.25 mmol) and N-hydroxysuccinimide (0.25 mmol) in DMF (1 mL) was cooled in an ice-bath, and then, diisopropylcarbodiimide (0.25 mmol) was added. The reaction mixture was allowed to warm to room temperature. After the reaction was stirred for 18 hours, the reaction mixture was transferred to another flask containing a slurry of glucosamine hydrochloride (0.25 mmol) and triethylamine (0.50 mmol), and the resulting mixture was stirred for 18 hours. Volatiles were removed in vacuo, and the residue separated by Si-gel column chromatography using 5% aqueous MeCN to yield the desired compound TP017 in the scheme above.

TP023 and TP029 were synthesized following a modification of the process described above. The acid was converted to the acid chloride using oxalyl chloride and a drop of DMF. Following 10 min of stirring Volatiles were removed and a solution of pentafluorophenol and NEt$_3$ in dichloromethane was added to it. After stirring for 30 min volatiles were removed in vacuo and the residue was dissolved in DMF and transferred to a a solution of glucosamine hydrochloride and NEt$_3$ in DMF/H$_2$O. The mixture was stirred for 18 hours, volatiles removed in vacuo and separated on Si-gel column using 10% aqueous MeCN to yield the title compounds.

G. Synthesis of Amine Linked glucosamine 4-iodobenzyl Oligoethyleneglycol Conjugates Amine linked glucosamine 4-iodobenzyl oligoethyleneglycol conjugates can be made in accordance with the synthetic scheme below by oxidation of oligoethyleneglycol mono-4-iodobenzyl ethers to the corresponding aldehydes, and reductive amination of monosaccharides using the oligoethyleneglycol aldehydes.

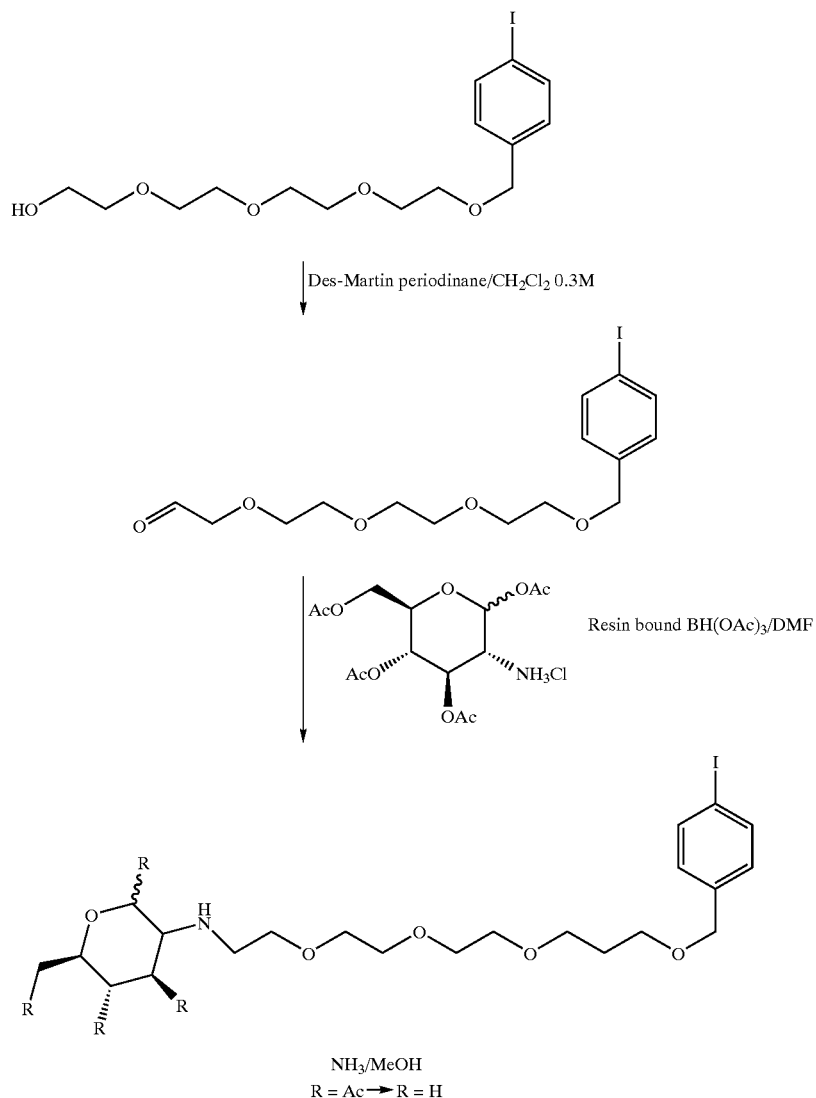

Thus, triethyleneglycol mono-4-iodobenzylether (0.55 mmol) is reacted with a 0.3 M solution of Des-Martin periodinane in dichloromethane (2.0 mL). After 1 hour, the solid precipitate is removed by filtration, volatiles are removed in vacuo, and the residue extracted with ether (3×10 mL). After removal of the volatiles, the residue is again extracted with (5×1 mL) ether, and removal of volatiles yields the product.

Tetraethyleneglycol mono-4-iodobenzylether and pentaethyleneglycol mono-4-iodobenzylether are similarly converted to the corresponding mono-4-iodobenzyl ethers.

The aldehydes are then converted to the desired compound as follows. To a slurry of tetraacetyl glucosamine hydrochloride (1 mmol) in DMF (5 mL) is added resin bound triacetoxyborohydride (2 mmol/g, 3 mmol) and the aldehyde (1 mmol). After the reaction is stirred for 18 hours, the solution is filtered, and the residue separated on a Si-gel column to yield the protected amine which is deprotected in methanolic ammonia to yield desired compound.

H. Synthesis of Pipsyl Glucosamine (Compound TP020) and Pipsyl Galactosamine

Pipsyl glucosamine (Compound TP020) can be made in accordance with the synthetic scheme below.

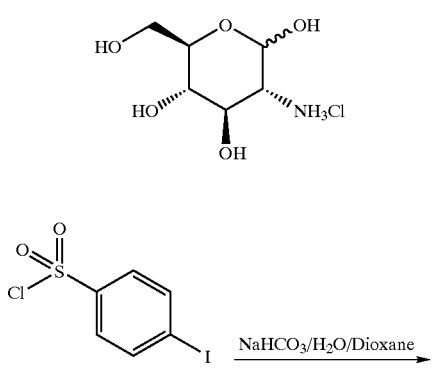

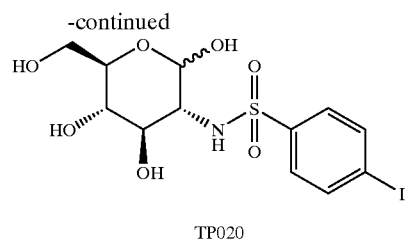

TP020

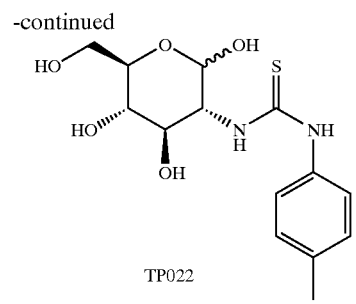

TP022

Thus, to a solution of glucosamine hydrochloride (1 mmol) in aqueous NaHCO$_3$ (2 mmol in 1 mL) was added a solution of pipsyl chloride (1 mmol) in dioxane (1 mL). The reaction mixture was stirred for 1 hour and then extracted with ether (3×5 mL); volatiles were removed in vacuo, and the residue crystallized from hot water to yield the product (compound TP020 in the scheme above) as a white solid. TP020 is generally illustrative of the compounds of the invention in which the linker is NHSO2 and particularly illustrative of the compounds of the invention that are iodo-substituted benzenesulfonyl glucosamines.

Pipsyl galactosamine is prepared following a similar procedure, using galactosamine instead of glucosamine.

Glucosamine hydrochloride, mannosamine hydrochloride and galactosamine hydrochloride is similarly converted to the respective 4-iodosulfenyl derivatives by a reaction with 4-iodosulfenyl chloride, following a protocol discussed above

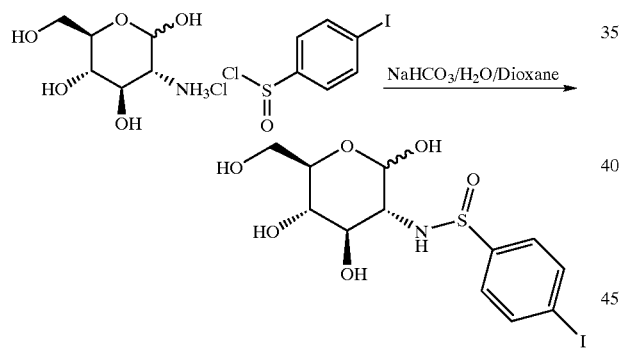

I. Synthesis of 4-(iodophenyl)thiocarbamoyl glucosamine (Compound TP022) and 4-(iodophenyl)thiocarbamoyl galactosamine 4-(Iodophenyl)thiocarbamoyl glucosamine (Compound TP022) was made in accordance with the synthetic scheme below.

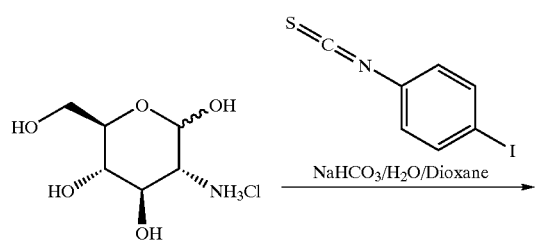

Thus, to a solution of glucosamine hydrochloride (1 mmol) and sodium bicarbonate (1 mmol) in water (1.0 mL) was added solution of 4-iodophenylisothiocyanate (1 mmol) in dioxane (1 mL), and the reaction was stirred for 18 hours. The reaction mixture was extracted with ether (3×5 mL), and the residue was then extracted with MeCN (5 mL). Removal of volatiles in vacuo yielded the desired compound (compound TP022 in the scheme above) as a foamy yellow solid.

The 4-(iodophenyl)thiocarbamoyl galactosamine derivative is prepared following a similar procedure, using galactosamine instead of glucosamine.

J. Synthesis of Hydroxyurea Glucosamine

Hydroxyurea glucosamine can be made in accordance with the synthetic scheme below.

Thus, a slurry of O-benzyl hydroxylamine (1 mmol) in DMF (5 mL), NEt$_3$ (2 mmol), and carbonyldiimidazole (1 mmol) is stirred for 1 hour. To this mixture is added glucosamine hydrochloride (5 mmol), and the reaction mixture is stirred for 18 hours. The solution is then filtered, volatiles removed in vacuo, and the residue separated using Si-gel chromatography with MeCN—10% aq MeCN as the eluent to yield compound 1 in the scheme above.

Then, to a solution of compound 1 in the scheme above, in MeOH, is added 10% Pd-C in the presence of H$_2$ for reduction. Filtration to remove the catalyst and concentration of the solution under reduced pressure yields the desired final compound, hydroxyurea glucosamine. Similarly an 'elongated' hydroxyurea glucosamine can be synthesized as outlined in the scheme below

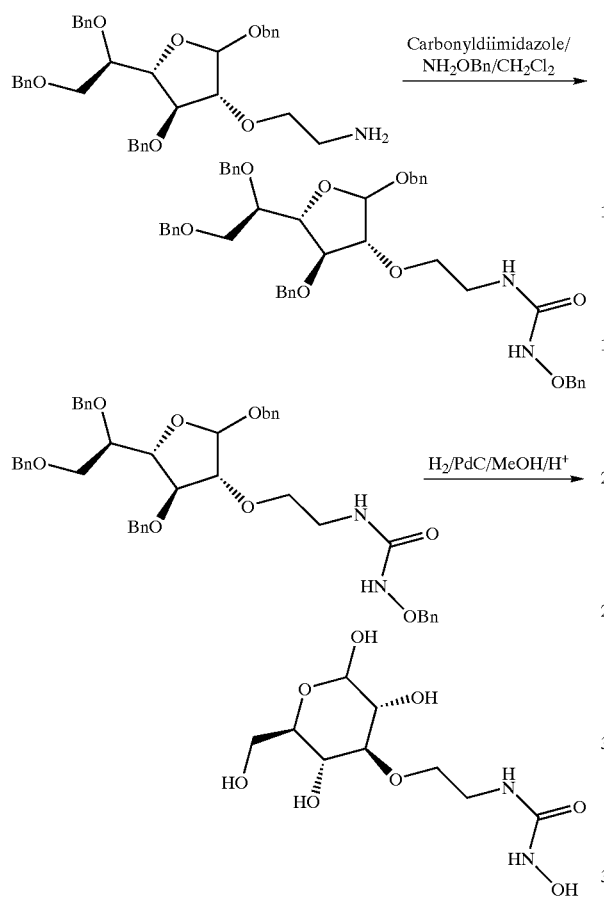

K. Iodine Exchange to Form the Radioactively-Labeled Conjugate

The following methods of the invention provide alternate routes to a radioactively labeled conjugate of the invention, and the intermediates generated in these routes are important compounds of the invention. While the methods are illustrated with reference to TP010, any of the numerous conjugates of the invention illustrated in this Example can be converted to their radioactive counterparts in accordance with these methods.

Iodine exchange can be conducted with the non-radioactive iodo-glucose conjugates of the invention to replace the non-radioactive iodo moiety with a radioactive iodine isotope. Iodoaryl glucose conjugates are first converted into a trimethyl tin (stannane) derivative. Then, the trimethyl tin is replaced by $I^{131}$ or any other isotope of iodine, as is known in the art for other compounds. For example, method suitable for the compounds of the present invention has been used to convert an aryl iodide to an aryl trimethyl stannane using hexamethylditin and a palladium catalyst in an inert solvent such as dioxane (see the references Harapanhalli et al., 1996, *J. Med. Chem.* 39: 4804–4809 and Wigerinck et al., 1993, *J. Med. Chem.* 36: 538–543). The conversion of glucosamine iodoaryl conjugates can be done in an analogous manner, although DMF can be substituted for dioxane for solubility. Alternatively, the glucosamine conjugate can be persilyated with a trimethylsilyating agent, such as bis trimethylsilyl trifluoroacetamide in DMF, followed by evaporation under reduced pressure and then solubilization in dioxane for the tin exchange reaction, as described in the references cited above. The trimethylsilyl groups are then removed using methanol or methanol-water mixtures.

The radiolabeling of the trimethyltin derivative via tin-iodine exchange with a radioactive isotope of iodine can be performed by the lactoperoxidase procedure as described in the Harapanhalli et al. reference cited above. A bromine moiety in an intermediate compound of the invention (for example 4-bromo-N-benzoyl-glucosamine) can be converted to the corresponding iodo conjugate (for example $^{131}$I-TP010) by a method of the invention adapted from the reference Klapars et al., 18 Dec. 2002, *J. Am. Chem. Soc.* 124(50): 14844–5). Alternate synthetic methods of the invention to make radioactively-labeled iodine containing conjugates of the invention are shown below, using the $^{131}$I-TP010 as an illustsrative example.

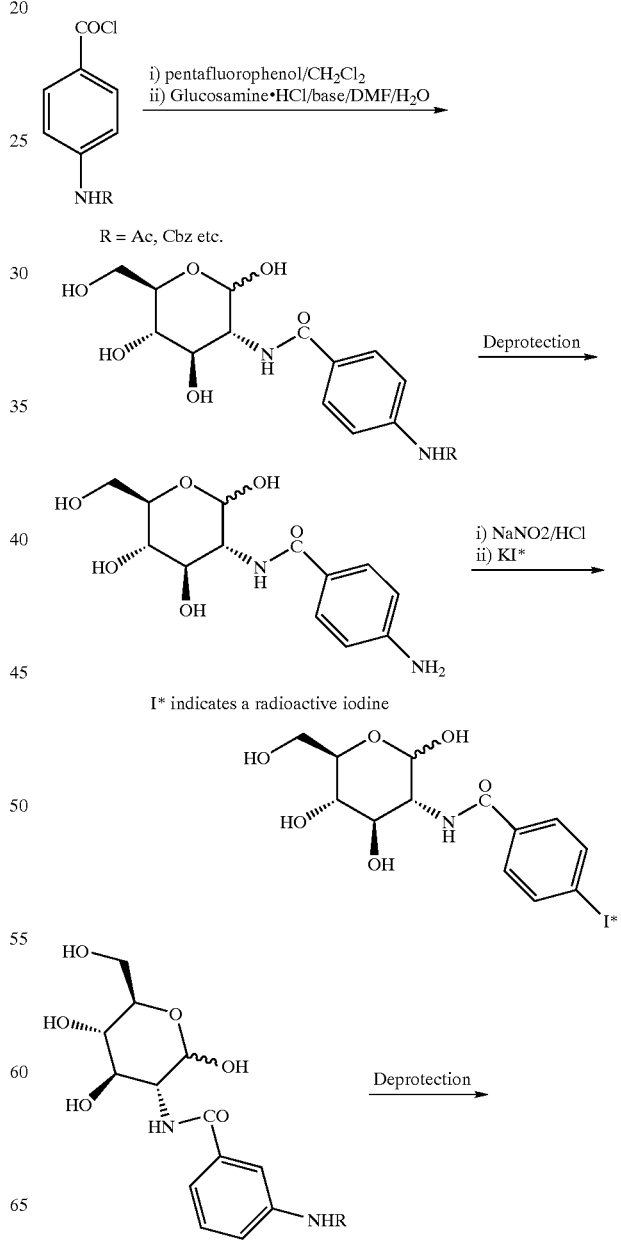

-continued

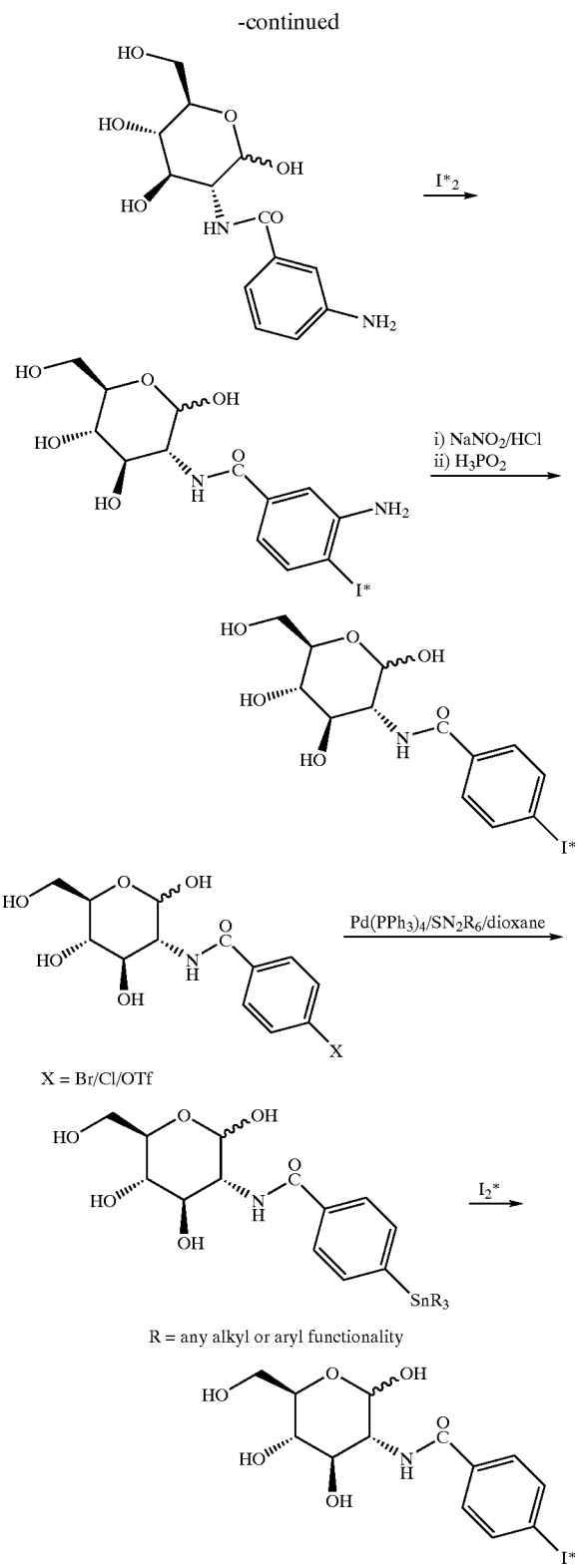

X = Br/Cl/OTf

R = any alkyl or aryl functionality

Radioactively-labeled $^{131}$I-TP010 can also be made via the following isotope exchange processes of the invention as well; other radioactively-labeled iodo conjugates of the invention can be made following similar methodology.

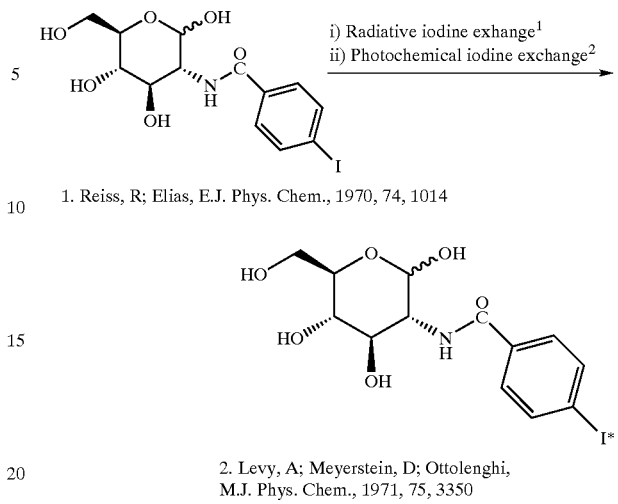

1. Reiss, R; Elias, E.J. Phys. Chem., 1970, 74, 1014

2. Levy, A; Meyerstein, D; Ottolenghi, M.J. Phys. Chem., 1971, 75, 3350

L. Dosing and Administration of Iodo-Containing Conjugates

Radioactively-labeled conjugates of the invention can be administered as a single bolus or via an extended infusion method or by repeated injections over a span of days or weeks. If multiple treatments are employed, then the radiotherapeutic dosing will be separated by a suitable interval, such as a period from four to twelve weeks. If low doses are used, then the interval can be shortened accordingly, such as to one or two weeks.

A high dose protocol of the invention delivers a dose in the range of 200 to 600 cGy or higher to the whole body and may require bone-marrow replacement therapy. Low-dose protocols of the invention, in which a dose in the range of 1 to 200 cGy, 10 to 100 cGy, 35 to 85 cGy, or 65 to 75 cGy, are typically more preferred for that reason. An amount of radioactivity that would provide approximately 500 cGy to the whole body can be estimated at about 825 mCi of $^{131}$I. The amount of radioactivity administered in accordance with the methods of the invention depends on whether the conjugate is being used for therapy or imaging. For therapeutic regimens using $^{131}$I, 1 to 1500 mCi (per 70 kg human subject), more typically 1 to 500 mCi, 10 to 200 mCi, or 40 to 120 mCi, are employed, and a high specific activity of the conjugate is desired. For diagnostic purposes, of course, much smaller amounts of radioactivity are employed, and a much lower specific activity is acceptable.

While the invention has been illustrated with respect to the anti-neoplastic agent $^{131}$I, the conjugates of the invention include other radioactive agents, such as $^{9}$Tc, $^{111}$In, $^{123}$I, $^{186}$Re, $^{188}$Re, $^{153}$Sm, $^{212}$Bi, $^{32}$P, and radioactive isotopes of Lu.

EXAMPLE 9

Uptake of Iodo-Containing Conjugates

This example describes assays conducted to determine to what extent certain iodo-containing conjugates of the invention are taken up or transported into cancer cells. As a positive control, the uptake of $^{14}$C-labeled-2-deoxy-D-glucose, a compound transported into human cells via glucose transporters and phosphorylated by hexokinase, and thus retained in the cell, was measured. As a negative control, the uptake of $^{14}$C-labeled-3-O-methyl-glucose, which is transported into the cell via the glucose transporters but is not phosphorylated and so is not retained, was measured.

The control assay was conducted as follows. HepG2 cells were plated at a density of $2\times10^5$ cells per well into a 24 well plate, and the plates were maintained in 37° C. incubator (5% $CO_2$) for 2 days. Prior to the uptake assay, the HepG2 cells were rinsed twice with pre-warmed (37° C.) phosphate-buffered saline (PBS) containing 1 mM $CaCl_2$, 1 mM $MgCl_2$ and 0.3% BSA. The rinsed HepG2 cells were then incubated with 270 µl of buffer (PBS/Ca/Mg/BSA) in the absence or presence of D-glucose (10 mM), L-glucose (10 mM), cytochalasin B (10 µM) or phloretin (0.3 mM) for 10 min at 37° C. Then, 30 µl of $^{14}C$-2DG (final concentration: 100 µM, 0.1 µCi) were added to each well, and the cells were incubated for 1 hour at 37° C. The plate was placed on ice, and the cells were washed rapidly three times with cold PBS buffer (4° C.) containing 1 mM $CaCl_2$ and $MgCl_2$. The cells were then lysed with 150 µl of 1% Triton X-100, and the lysate was transferred to a scintillation vial. The well was rinsed with 200 µl $ddH_2O$, and the rinsate was transferred to the same vial. Radioactivity was quantified using a scintillation counter. The protein concentration of each sample was determined using a BCA kit (Sigma, St Louis, Mo.). The amount of uptake of $^{14}C$-2DG is reported below in units of nmole/mg protein/60 min.

To measure uptake of the iodo-containing compounds of the invention, HepG2 cells were plated at a density of $2\times10^5$ cells per well into a 24 well plate, and the plates were maintained in 37° C. incubator (5% $CO_2$) for 2 days. Prior to the uptake assay, the HepG2 cells were rinsed twice with pre-warmed (37° C.) phosphate-buffered saline (PBS) containing 1 mM $CaCl_2$, 1 mM $MgCl_2$ and 0.3% BSA. The HepG2 cells were then incubated with 270 µl of buffer (PBS/Ca/Mg/BSA) in the absence or presence of D-glucose (10 mM), L-glucose (10 mM), cytochalasin B (10 µM) or phloretin (0.3 mM) for 10 min at 37° C. Then, 30 µl of each of the conjugates (final concentration: 100 µM) were added to individual test wells, and the plates were incubated for 1 hour at 37° C. The plate was placed on ice, and then, the cells were washed rapidly three times with cold PBS buffer (4° C.) containing 1 mM $CaCl_2$ and $MgCl_2$. The cells were lysed by the sequential addition of 150 µl of 1% Triton X-100 and 100 µl of $ddH_2O$ into each well. Lysates from six replicate wells were pooled together for each sample (volume per sample: 1.5 ml). The protein concentration of each sample was determined using a BCA kit (Sigma, St Louis, Mo.). Samples were diluted by addition of 4 ml of $ddH_2O$ (final volume per sample: 5.5 ml), and the samples treated with the iodo-containing conjugates were analyzed for iodide content by inductively coupled plasma-mass spectrometry (West Coast Analytical Service, Santa Fe Spring, Calif.). The amount of uptake of iodide-containing glucose conjugate is reported as nmole/mg protein/60 min. Results of various assay for various compounds described in Example 8 are reported in Table 1 below.

TABLE 1

Uptake of Compounds by HepG2 Cells

| Compound | Uptake (nmole/mg/60 min) |
| --- | --- |
| 2-DG | 51.8 +/− 4.3 (n = 3) |
| 3-O-Methyl Glucose | 0.2 |
| TP010 | 2.7 +/− 0.7 (n = 5) |
| TP011 | 0.5 |
| TP012 | 2.8 +/− 0.14 (n = 4) |
| TP014 | 1.2 |

TABLE 1-continued

Uptake of Compounds by HepG2 Cells

| Compound | Uptake (nmole/mg/60 min) |
| --- | --- |
| TP015 | 1.65; 1.64 |
| TP016 | 0.5 |
| TP017 | 0.16; 0.18 |
| TP018 | 2.28; 2.31 |
| TP019 | 1.39; 1.00 |
| TP020 | 0.83; 0.81 |
| TP021 | 0.64; 0.61 |
| TP022 | 0.90; 0.97 |
| TP023 | 0.46; 0.48 |
| TP024 | 0.40; 0.39 |
| TP025 | 0.83; 0.87 |
| TP026 | 0.47; 0.54 |
| TP027 | 0.68; 0.99 |
| TP028 | 0.99; 1.12 |
| TP029 | 0.19; 0.17 |

These results indicate that the compounds TP010, TP012, and TP018 were, among the compounds of the invention tested, the compounds most taken up by the cells. The uptake of compounds TP010 and TP011 was blocked by the addition of D-glucose and not L-glucose, indicating that the uptake of these compounds by the HepG2 cells was via a glucose transporter. The uptake of compound TP012 was not blocked by D-glucose or L-glucose.

EXAMPLE 10

This example illustrates the preparation of representative pharmaceutical formulations for oral administration.

| A. | Ingredients | % wt./wt. |
| --- | --- | --- |
| | conjugate | 20.0% |
| | Lactose | 79.5% |
| | Magnesium stearate | 0.5% |

The above ingredients are mixed and dispensed into hard-shell gelatin capsules containing 100 mg each, one capsule would approximate a total daily dosage.

| B. | Ingredients | % wt./wt. |
| --- | --- | --- |
| | conjugate | 20.0% |
| | Magnesium stearate | 0.9% |
| | Starch | 8.6% |
| | Lactose | 79.6% |
| | PVP (polyvinylpyrrolidine) | 0.9% |

The above ingredients with the exception of the magnesium stearate are combined and granulated using water as a granulating liquid. The formulation is then dried, mixed with the magnesium stearate and formed into tablets with an appropriate tableting machine.

| C. | Ingredients | |
| --- | --- | --- |
| | conjugate | 0.1 g |
| | Propylene glycol | 20.0 g |

-continued

| C. | Ingredients | |
|---|---|---|
| | Polyethylene glycol 400 | 20.0 g |
| | Polysorbate 80 | 1.0 g |
| | Water q.s. | 100 mL |

The 2-conjugate is dissolved in propylene glycol, polyethylene glycol 400 and polysorbate 80. A sufficient quantity of water is then added with stirring to provide 100 mL of the solution which is filtered and bottled.

| D. | Ingredients | % wt./wt. |
|---|---|---|
| | conjugate | 20.0% |
| | Peanut Oil | 78.0% |
| | Span 60 | 2.0% |

The above ingredients are melted, mixed and filled into soft elastic capsules.

EXAMPLE 11

This example illustrates the preparation of a representative pharmaceutical formulation for parenteral administration.

| Ingredients | |
|---|---|
| conjugate | 0.02 g |
| Propylene glycol | 20.0 g |
| Polyethylene glycol 400 | 20.0 g |
| Polysorbate 80 | 1.0 g |
| 0.9% Saline solution q.s. | 100 mL |

The 2-conjugate is dissolved in propylene glycol, polyethylene glycol 400 and polysorbate 80. A sufficient quantity of 0.9% saline solution is then added with stirring to provide 100 mL of the I.V. solution which is filtered through a 0.2.mu. membrane filter and packaged under sterile conditions.

EXAMPLE 12

This example illustrates the preparation of a representative pharmaceutical composition in suppository form.

| Ingredients | % wt./wt. |
|---|---|
| conjugate | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 13

This example illustrates the preparation of a representative pharmaceutical formulation for insufflation.

| Ingredients | % wt./wt. |
|---|---|
| Micronized conjugate | 1.0% |
| Micronized lactose | 99.0% |

The ingredients are milled, mixed, and packaged in an insufflator equipped with a dosing pump.

EXAMPLE 14

This example illustrates the preparation of a representative pharmaceutical formulation in nebulized form.

| Ingredients | % wt./wt. |
|---|---|
| conjugate | 0.005% |
| Water | 89.995% |
| Ethanol | 10.000% |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for treating a cancer selected from the group consisting of lung cancer, breast cancer, colon cancer, ovarian cancer, cervical cancer, bladder cancer, head and neck cancer, skin cancer and melanoma and low and intermediate grade non-Hodgkin's Lymphoma in a subject, said method comprising administering to said subject an effective amount of a glucose-anti-neoplastic agent conjugate having the formula:

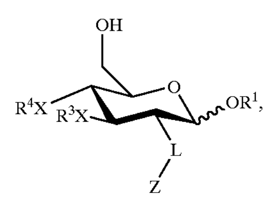

wherein L is selected from the group consisting of a bond, alkenyl, alkylamine, alkylether, amide, carbamate, urea, thiocarbamate, thiourea, and combinations thereof; and Z is an anti-neoplastic agent selected from the group consisting of a radionuclide selected from the group consisting of Yttrium-90, Iodine-125, Iodine-131, and Phosphate-32; an iodoaryl group bearing an Iodine-131; hydroxyurea; 3-aminopyridine-2-carboxaldehyde thiosemicarbazone; 5-hydroxypyridine-2-carboxaldehyde thiosemicarbazone; camptothecin and its analogs; carboplat and its analogs; DOTA: methotrexate and its analogs; mitoxantrone, doxorubicin, idarubicin, balrubicin, eprubicin, imatinib, dacarbazine and procarbazine; and mitomycin; each X is independently selected from the group consisting of O and NH; and $R^1$, $R^3$ and $R^4$ are each members independently selected from the group consisting of H, ($C_1$–$C_{12}$)alkyl and ($C_1$–$C_{12}$)acyl.

2. A method in accordance with claim 1, wherein Z is 4-$^{131}$iodobenzene.

3. A method in accordance with claim 1, wherein said glucose-anti-neoplastic agent conjugate has the formula:

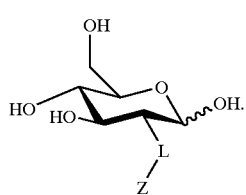

4. A method in accordance with claim 1, further comprising administering at least one additional anti-neoplastic agent.

5. A method of claim 4, wherein said at least one additional anti-neoplastic agent is a member selected from the group consisting of cyclophosphamide, doxorubicin, prednisone and cisplatin.

6. A method in accordance with claim 1, wherein said cancer is selected from the group consisting of relapsed cancer and refractory cancer.

7. A method in accordance with claim 1, further comprising a preliminary step of reducing glucose ingestion in said subject.

8. A compound of structure:

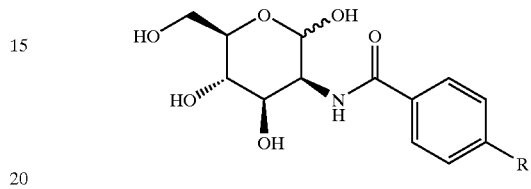

wherein R is $SnX_3$, wherein X is independently selected from the group consisting of a linear or branched $C_1$–$C_6$ alkyl, Br, triflate ($OSO_2CF_3$), amino, and a protected amino group.

* * * * *